(12) United States Patent (10) Patent No.: US 8,512,227 B2
Murakami et al. (45) Date of Patent: Aug. 20, 2013

(54) APPARATUS FOR ASSISTING OPERATIONS OF MEDICAL INSTRUMENT ATTACHED TO ENDOSCOPE

(75) Inventors: Kazushi Murakami, Tokyo (JP); Yoshio Onuki, Tokyo (JP); Takaaki Komiya, Tokyo (JP); Yasuhito Kura, Tokyo (JP); Takehiro Nishiie, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1428 days.

(21) Appl. No.: 11/588,578

(22) Filed: Oct. 27, 2006

(65) Prior Publication Data

US 2007/0100254 A1 May 3, 2007

(30) Foreign Application Priority Data

Oct. 27, 2005 (JP) .................................. 2005-313457

(51) Int. Cl.
*A61B 1/00* (2006.01)
*A61B 1/04* (2006.01)

(52) U.S. Cl.
USPC ............ 600/106; 600/104; 600/114; 600/118

(58) Field of Classification Search
USPC ......................................... 600/106, 131, 118
See application file for complete search history.

(56) References Cited

U.S. PATENT DOCUMENTS

| | | | | |
|---|---|---|---|---|
| 4,222,380 A | * | 9/1980 | Terayama | 604/115 |
| 5,159,446 A | | 10/1992 | Hibino et al. | |
| 5,961,526 A | * | 10/1999 | Chu et al. | 606/113 |
| 6,872,178 B2 | * | 3/2005 | Weinberg | 600/114 |
| 2002/0087048 A1 | * | 7/2002 | Brock et al. | 600/114 |
| 2003/0212308 A1 | * | 11/2003 | Bendall | 600/131 |
| 2005/0267327 A1 | * | 12/2005 | Iizuka et al. | 600/106 |

FOREIGN PATENT DOCUMENTS

| | | |
|---|---|---|
| EP | 0 776 739 A2 | 6/1997 |
| EP | 1 253 509 A1 | 10/2002 |
| EP | 1 584 300 A2 | 10/2005 |
| JP | 57-190541 | 11/1982 |
| JP | 2000-000207 | 1/2000 |
| WO | WO 2007/002545 A1 | 1/2007 |

* cited by examiner

*Primary Examiner* — Alireza Nia
(74) *Attorney, Agent, or Firm* — Scully, Scott, Murphy & Presser, P.C.

(57) ABSTRACT

An apparatus is provided which assists operations required for a medical instrument. A tubular portion and a therapeutic member of the instrument are inserted through a channel of an insertion tube of an endoscope. In the apparatus, a first drive unit enables the therapeutic member to perform the desired therapeutic operations responsively to a first command signal and a second drive unit enables the tubular portion inserted in the channel to convey responsively to a second command signal. An input device is provided at which two kinds of commands are allowed to be inputted command by command. The two kinds of commands allow the therapeutic member and the tubular portion to be driven in parallel with each other. A controller provides the first and second drive units with the first and second command signals, respectively, in accordance with the two kinds of commands.

10 Claims, 38 Drawing Sheets

APPARATUS FOR ASSISTING OPERATIONS OF MEDICAL INSTRUMENT ATTACHED TO ENDOSCOPE

CROSS REFERENCE TO RELATED APPLICATION

The patent application related to and incorporates by reference Japanese Patent application No. 2005-313457 filed on Oct. 27, 2005.

BACKGROUND OF THE INVENTION

1. The Field of the Invention

The present invention relates to an operation-assisting apparatus for medical instruments and medical tools (hereinafter referred to as medical instruments), which is able to facilitate various manual operations to be done for those medical instruments attached to an endoscope for use, and in particular, to an operation-assisting apparatus directed to a medical instrument involving inserting (feeding) and pulling-out operations in and from a body cavity of an object being examined as well as therapeutic operations of a therapeutic member of the medical instrument.

2. Related Art

In the medical field, endoscopes have been used widely and become an indispensable medical tools. In general, an endoscope is provided with a thin and elongated insertion tube including a flexibly bendable section positioned at the distal end thereof and an operating body at which various operating devices such as knobs and switches are provided. Such operating devices are used by operators to issue commands for various operations of the endoscope.

An endoscope used in the medical field is able to insert its insertion tube into body cavities of an object. Since an observing optical system is disposed at the distal end of the insertion tube, tissue in the body cavities can be observed through the optical system. In addition, if necessary, medical instruments inserted through a therapeutic-instrument channel of the endoscope can be used for various therapeutic operations.

When it is required in a conventional endoscope that a therapeutic instrument be inserted into a body cavity through the therapeutic-instrument channel, an operator(s) has to feed the instrument into a body cavity, while still holding the medical instrument by the sheath. However, because the therapeutic instrument has a length as long as 2 meters, feeding (inserting) therapeutic instrument results in operations that need much work. Additionally, the feeding operations should be done so that the sheath is prevented from buckling and touching impure regions in the cavity. Hence, such situations make the feeding and therapeutic operations considerably more difficult.

In order to attempt to alleviate such difficulties, Japanese Patent Laid-open Publication No. 57 (1982)-190541 discloses an endoscope provided with an inserting/pulling apparatus that inserts and pulls out a therapeutic instrument into and from a therapeutic-instrument channel of the endoscope. In using this endoscope, the therapeutic instrument is mechanically inserted into the channel until the tip of the instrument is reached near the distal end of the insertion tube, and then the operations are switched to operator's manual operations. Thus, the operator is in charge of sensitive inserting operations after the instrument tip goes beyond the distal end of the tube and manually operates the instrument to allow the therapeutic member to be positioned in a controlled manner.

An alternative way is disclosed in Japanese Patent Laid-open Publication No. 2000-207, in which, in addition to a configuration to allow a therapeutic instrument to be inserted and pulled out into and from a therapeutic-instrument channel of an endoscope, there is provided an instrument-inserting/pulling apparatus with instrument operating means for operating a therapeutic member attached to the distal end of the instrument. This apparatus is provided with a foot switch used for commanding various operations for the apparatus.

However, in the case of the endoscope disclosed in the former known reference, an operator has to operate the therapeutic member by hand, although the sheath of the therapeutic instrument can mechanically be inserted into the therapeutic-instrument channel. In other words, for operating the therapeutic member, an operator has to be engaged in operating a slider positioned at an operation unit coupled with the base of the sheath of the instrument, while the operator still has to control various portions of the endoscope itself and the insertion/pulling-out operations of the sheath of the instrument. Hence the operations of the operator are very difficult.

In addition, this endoscope has no means for allowing the operator to fix or hold the operation unit of the instrument in a state where the sheath is in the therapeutic-instrument channel. This means that it is required that the operation block of the therapeutic instrument be gripped by an operator different from the operator who handles the therapeutic instrument.

Hence, for example, there is a case a doctor operates the endoscope and another person such as a nursing person is in charge of operating the therapeutic instrument. In this case, for realizing sensitive operations required for the therapeutic instrument, sufficient communication is needed between the doctor and the nursing person in order to operate the instrument properly in response to demands from the doctor. Such communication burdens heavily the people who are engaged in the operations.

Normally, with viewing endoscopic images from the endoscope, an operator inspects and treats a lesion being treated of an object. If the instrument-inserting/pulling apparatus disclosed by the latter known reference is adopted by the endoscope, an operator is obliged to see the foot switch for positional confirmation before stepping on the foot switch, whenever the therapeutic instrument is subjected to insertion/pulling operations and/or the therapeutic member is subjected to operations assigned thereto. In some cases the foot switch is equipped with a plurality of switches, selectively operating the plural switches or simultaneously operating plural ones of those plural switches becomes very difficult work for operators. Furthermore, operations made by foot also involve difficulties when sensitive and subtle operations are required in conveying the therapeutic instrument and operating the therapeutic member.

There is another difficulty in the configuration that uses the foot switch. Medical treatments on the endoscope frequently require other medical devices, such as devices utilizing high frequency signals, which receive commands from foot switches. In such a case, an operator(s) is required to operate those various foot switches for instrument-inserting/pulling apparatus and the other medial devices. Hence, such operations are heavy burdens on the operator(s) such as doctors.

SUMMARY OF THE INVENTION

The present invention has been made in consideration of the foregoing difficulties confronted by the conventional techniques, and has an object to provide an endoscope system capable of facilitating the operator's operations needed by a therapeutic instrument combined with an endoscope by assisting the operations.

The present invention provides, as one aspect, an apparatus for assisting operations required for a medical instrument having a tubular portion with a distal end and a therapeutic member attached to the distal end of the tubular portion for desired therapeutic operations for treatment, the tubular portion and the therapeutic member being inserted through a channel of an insertion tube of an endoscope, the apparatus comprising: a first drive unit configured to enable the therapeutic member to perform the desired therapeutic operations in response to a first command signal; a second drive unit configured to enable the tubular portion inserted in the channel of the insertion tube to convey along the channel in response to a second command signal; an input device at which two kinds of commands are allowed to be inputted command by command, the two kinds of commands allowing the therapeutic member and the tubular portion to be driven in parallel with each other; and a controller configured to provide the first and second drive units with the first and second command signals, respectively, in accordance with the two kinds of commands inputted at the input device.

DETAILED DESCRIPTION OF THE PREFERRED EMBODIMENTS

Various embodiments of the present invention will now be described with reference to the accompanying drawings.

First Embodiment

With reference to FIGS. 1-20, a first embodiment of an operation assisting apparatus according to the present invention, with which medical instruments used in combination with an endoscope are subjected to assistance of the operations thereof. In the present embodiment, the assisting apparatus is reduced into practice in an endoscope system, and will now be described with the endoscope system.

Figure 1:
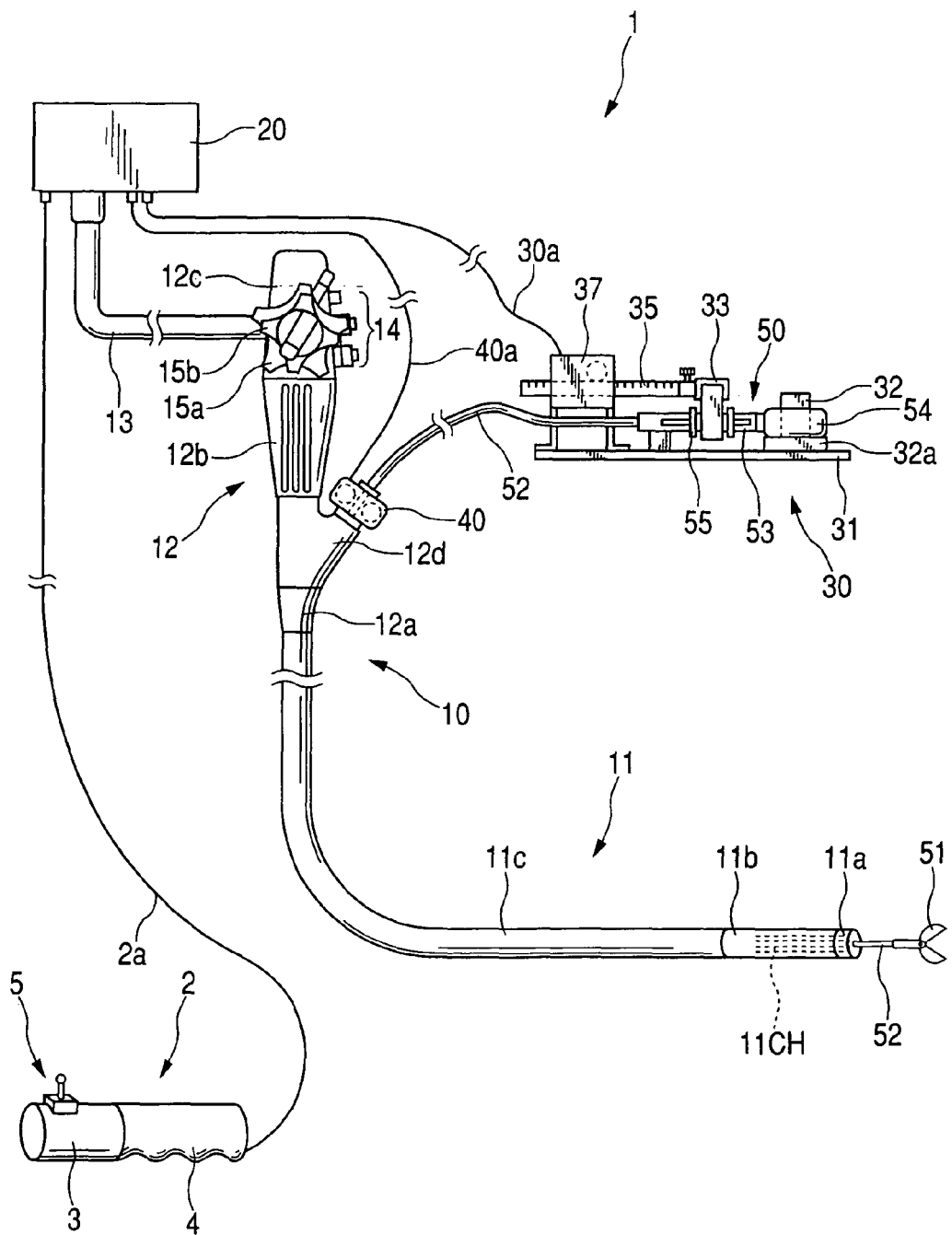
FIG. 1 is a schematic view showing the configuration of a main part of an endoscope system according to a first embodiment of the present invention.

As shown in FIG. 1, an endoscope system 1 according to the present embodiment is provided with, as essential components thereof, a manipulating unit 2 serving as an operating unit handled by operators, endoscope 10, a controller 20, an instrument operating unit 30 serving as a first drive unit, and an instrument conveying unit 40 serving as a second derive unit. The controller 20, which functions as a controller, is equipped with an endoscope processor described later, a light source unit (not shown), and a video processor (not shown). In these components, the controller 20, instrument operating unit 30, instrument conveying unit 40, and manipulating unit 2 compose the assisting apparatus for assisting operators who handle the endoscope system. Though not shown, the controller 20 is connected to display means, such as monitors, for displaying images acquired by the endoscope.

The endoscope 10 is provided with a thin and elongated insertion tube 11, an operating base holder 12 rigidly connected to a base end of the insertion tube 11, and a universal code 13 connecting the operating base holder 12 and the controller 20.

The insertion tube 11 is a soft tubular member composed of a distal section 11a, a flexibly bendable section 11b, and a flexible tubular section 11c, which are positioned and mutually rigidly connected in this order from the distal end thereof, but are flexible and bendable as a whole. Further, the operating base holder 12 is composed of a bend protection portion 12a to which a base end of the flexible tubular section 11c is rigidly connected, a grasping portion 12b provided with an instrument inlet structure 12d, and a main operation portion 12c connected to the base portion 12a via the grasping portion 12b. All the portions 12a to 12d are rigidly combined to form a single body that is the operating base holder 12. Of these, the main operation portion 12c is provided with bending levers 15a and 15b as well as plural switches 14 used for commanding air supply, water supply, suction, and various optical operations for imaging means and illuminating means disposed to the distal section 11a. The bending lever 15 is used to command a bend at the bendable section 11b.

In this endoscope 10, a therapeutic-instrument channel 11CH (thin and elongated tubular bore, through which various therapeutic instruments are inserted and pulled out (that is, conveyed), is formed to range from the instrument inlet structure 12d to the distal section 11a through the insertion tube 11, which will be detailed later. The universal code 13 has a base end at which a connector 13a is disposed for connection with the controller 20.

The manipulating unit 2 is equipped with an inner processing circuit eclectically connected with the controller 20 via a signal cable 2a compose of a coaxial cable. The instrument operating unit 30 is electrically connected to the controller 20 via an electric cable 30a and accepts a handle 53 of the therapeutic instrument 50 which serves as a medical instrument such as a biopsy forceps.

In the same way, the instrument conveying unit 40 is eclectically connected to the controller 20 via another electric cable 40a and secured at the instrument inlet structure 12d of the endoscope 10. The therapeutic instrument 50 has a tubular sheath 52 and an operating wire 52a passing through the sheath 52. The sheath 52 and the operating wire 52a compose a tubular portion of the instrument 50 and the tubular portion, that is, the sheath 52 (together with the operating wire 52a), inserted in the therapeutic-instrument channel 11CH.

The therapeutic instrument 50 comprises a therapeutic member 51 located at the distal end thereof, the operating wire 52a of which one end is coupled with the therapeutic member 51 for operations, the tubular sheath 52 containing therein the operating wire 52a such that the wire 52a passes through the sheath 52 and is rotatable about an axis of the wire 52a, and the foregoing handle 53 coupled with the other end of the operating wire 52a. For use of the therapeutic instrument 50, this instrument 50 is subjected to its inserting and pulling-out operations into a body cavity of an object being examined. Such inserting and pulling-out operations are carried out by making the sheath 52 insert and pull out, as will be described. Thus inserting and pulling out the sheath 52 means that the operating wire 52a contained in the sheath 52 and the therapeutic member 51 located at the distal end are inserted and pulled out together with the sheath 52.

Through the instrument conveying unit 40, the sheath 52 (together with the operating wire 52a) of the therapeutic instrument 50 is driven to be guided into the therapeutic-instrument channel 11CH.

In the present embodiment, the therapeutic instrument 50 is exemplified as the biopsy forceps, as stated above, so that the therapeutic member 51 is composed by the grip portion of the biopsy forceps. The sheath 52 of this therapeutic instrument 50 is inserted into the channel 11CH in such a manner that the sheath 52 is made to freely advance and go back, thus making it possible for the therapeutic member 51 to appear from and disappear into the opening of the channel 11CH in the front of the distal section 11a of the insertion tube 11.

Figure 2:
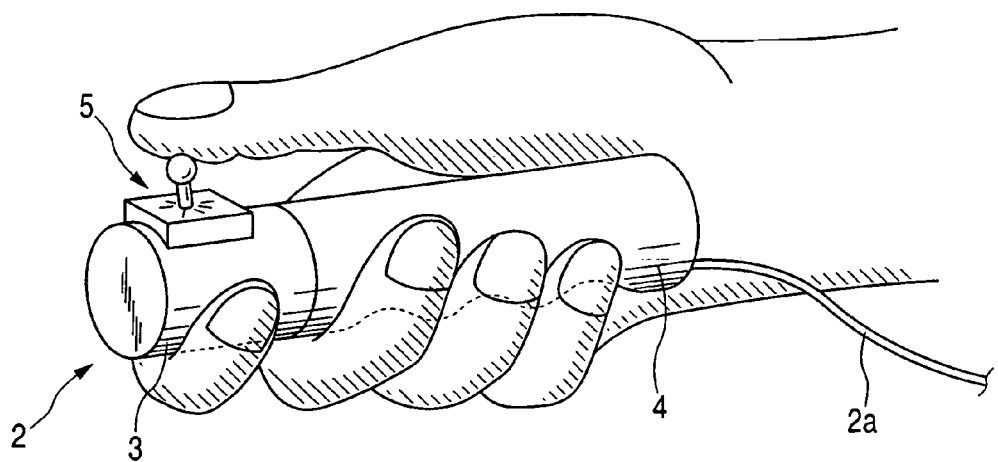
FIG. 2 is a perspective view showing the appearance of a manipulating unit employed by the endoscope system.
Figure 3:
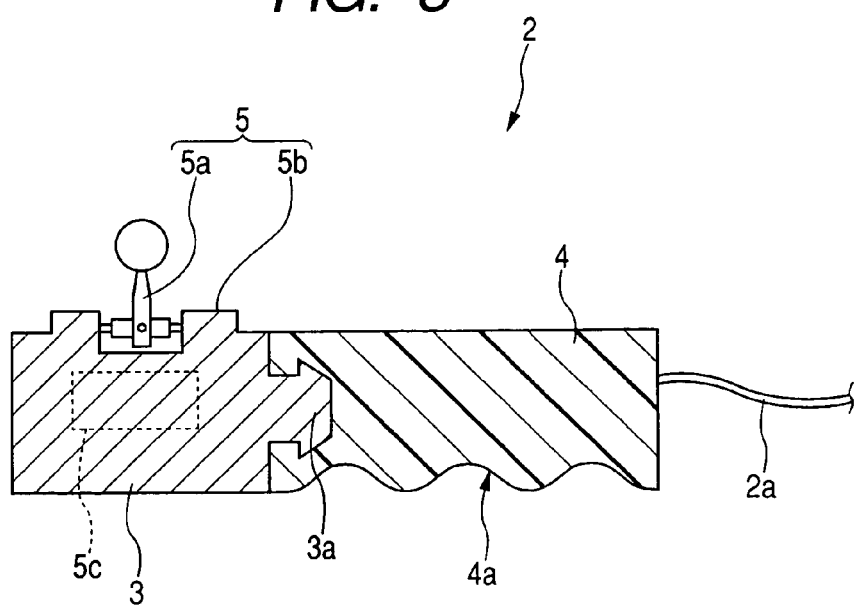
FIG. 3 is a sectional view of the manipulating unit, which is sectioned along a longitudinal direction of the manipulating unit.

With reference to FIGS. 2 and 3, a detailed description will now be made to the manipulating unit 2.

As shown in FIG. 2, the manipulating unit 2 is as a whole shaped into a substantially cylindrical member comprising a hard body 3 and a grip 4 coupled with the body 3. The grip 4 is formed of elastic material and has a base end from which the signal cable 2a extend outside.

The body 3 has an outer circumferential surface in and on which an input device 5 is disposed. This input device 5 receives operator's input operations to be done for operating the therapeutic instrument 50. The input device 5 has an operation lever 5a which is a joystick type, 2-axis operable and origin-return switch, a lever support 5b supporting the operation lever 5a, and a processing circuit 5c. The operation lever 5a and lever support 5b compose an operating member and the processing circuit 5c composes an output member. The processing circuit 5c has an electric circuit to electrically detect an amount of operation (including an operated angle) done at the operation lever 5a as changes in such physical quantities as resistance, light and magnetism. The detected results are sent, as an electric output signal, from the processing circuit 5b to the controller 20.

The body 3 is rigidly linked with the grip 4 via a fitting mechanism in which a protrusion 3a from the base-side back surface are fitted with a fitting hole formed on the distal-side front surface, as shown in FIG. 3. The grip 4, which is gripped by an operator's one hand, as shown in FIG. 2, is formed to have a wave-shaped (in a longitudinal section) outer surface 4a for making operator's grip of the manipulating unit 2 easier. The wave-shaped outer surface 4 is positioned to be opposite to the input device 5 about the longitudinal axis of the grip 4.

Incidentally, in the configuration of the manipulating unit 2 shown in FIGS. 2 and 3, a leftward direction toward the body 3 is called an distal end side, a rightward direction toward the grip is called a base end side, the upper side on which the input device 5 is disposed is called an upper side (or upper), and the lower side on which the wave-shaped outer surface 4a is formed is called a lower side (or lower).

Figure 4:
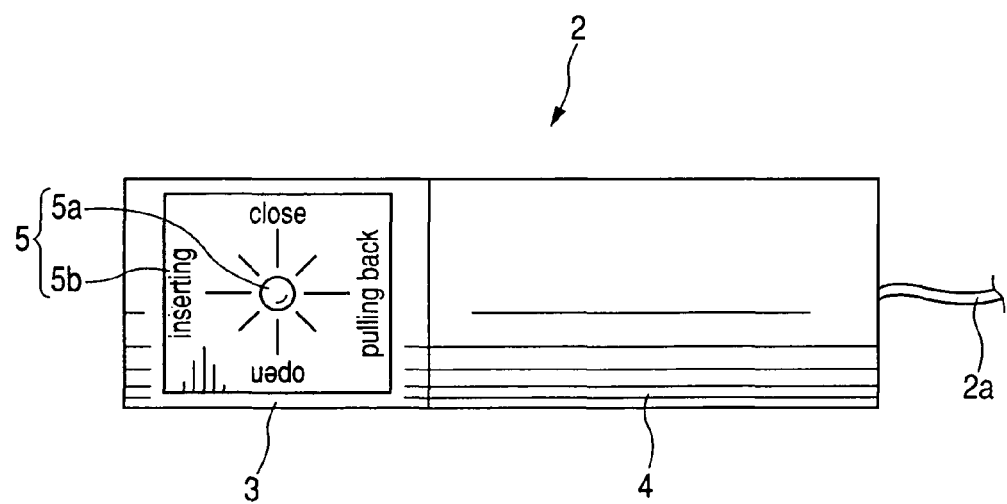
FIGS. 4 and 5 are plan views each showing the manipulating unit.
Figure 5:
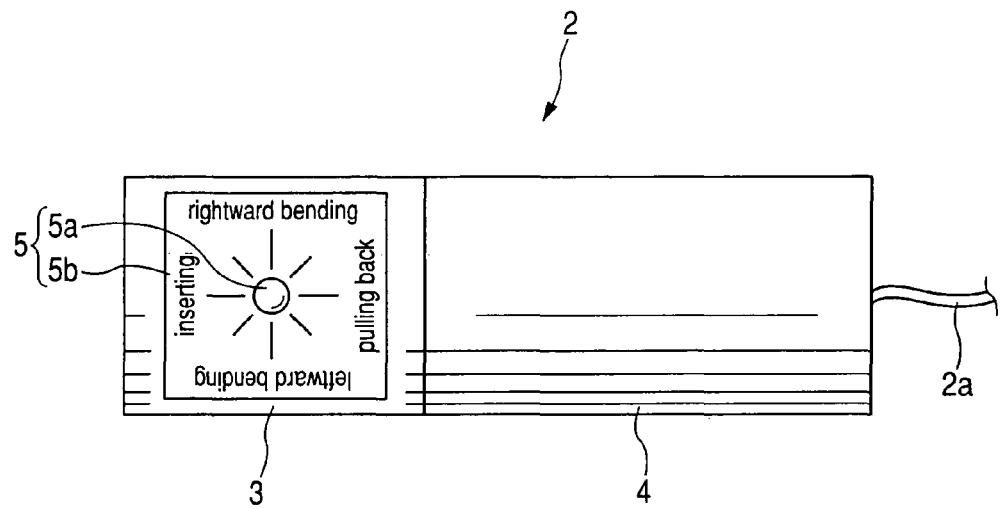

As additionally shown in FIGS. 4 and 5, on the upper surface of the lever supporter 5b, markings indicative of tilt directions in which the operation lever 5a are tilted selectively are engraved.

One example of such tilt-direction markings is shown in FIG. 4, wherein there are engraved four markings consisting of a marking "inserting" on the distal end (frontal) side, a marking "pulling back" on the base end (rear) side, a "open" on the left side when advancing toward the distal end and looking down the upper surface (in FIG. 4, the lower side), and a marking "close" on the right side when advancing toward the distal end and looking down the upper surface (in FIG. 4, the upper side).

Another example is shown in FIG. 5, wherein there are also engraved four tilt-direction markings on the upper surface of the lever support 5b, which are a marking "inserting" on the distal end (forward) side, a marking "pulling back" on the base end (backward) side, a marking "leftward bending" on the leftward side (the lower side in FIG. 5), and a marking "rightward bending" on the rightward side (the upper side in FIG. 5).

As a matter of course, depending on the types of therapeutic instruments being used, these tilt-direction markings may be changed so that the markings are adaptive to the operations of each instrument.

Figure 6:
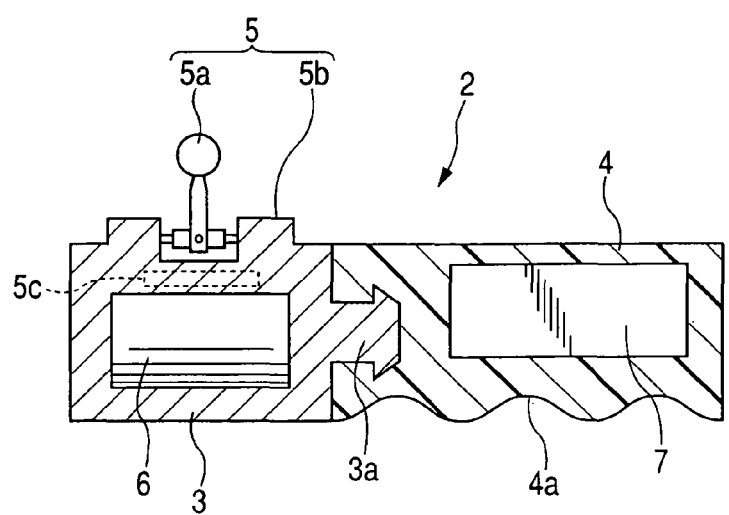
FIG. 6 is a longitudinally sectioned view of a manipulating unit according to a modification.

The foregoing manipulating device 2 is formed into a wired type and eclectically connected to the controller 20, but may be modified into a wireless type, as shown in FIG. 6. Specifically, the manipulating device 2 is provided with a transmitter 6 embedded within the body 3 and a battery 7 embedded within the grip 4 for power supply to the transmitter 6. In response to commands given at the input device 5, command singles are sent from the processing circuit 5c via the transmitter 6 to the controller 20. Incidentally, the controller 20 comprises a receiver (not shown) to receive the command signals from the transmitter 6.

Figure 7:
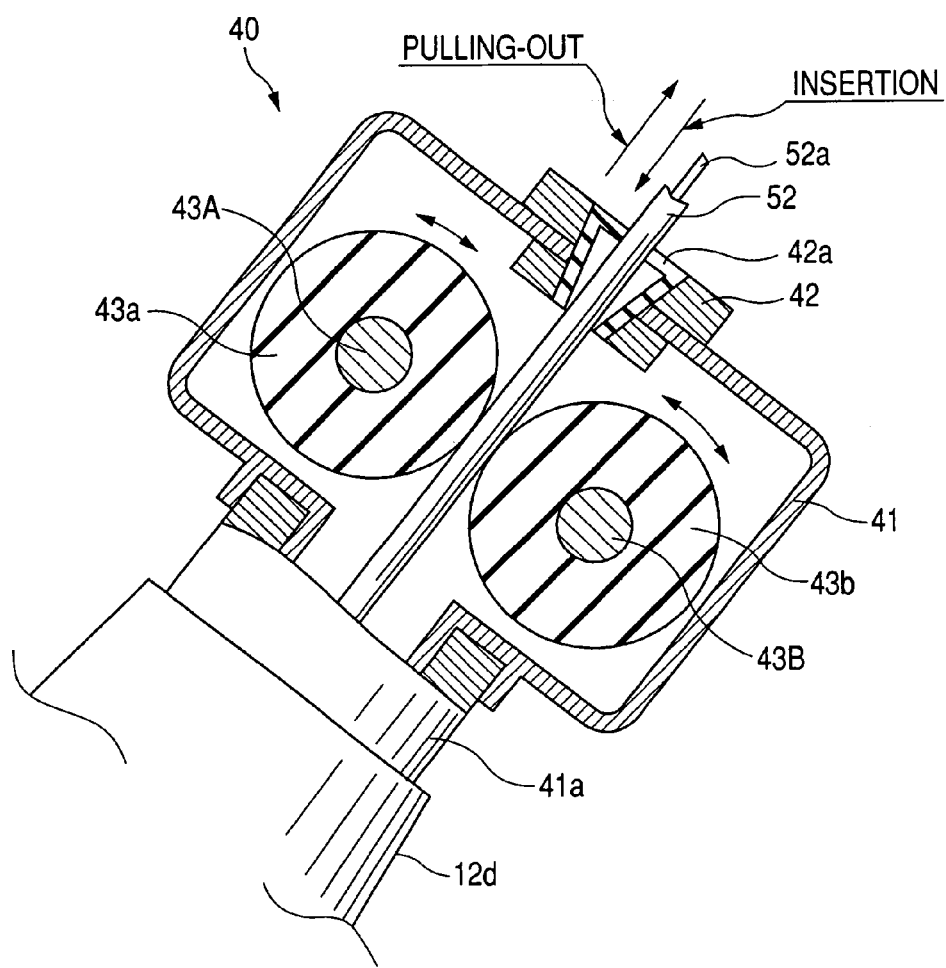
FIG. 7 is a longitudinally sectioned view of an instrument conveying unit employed the endoscope system.
Figure 8:
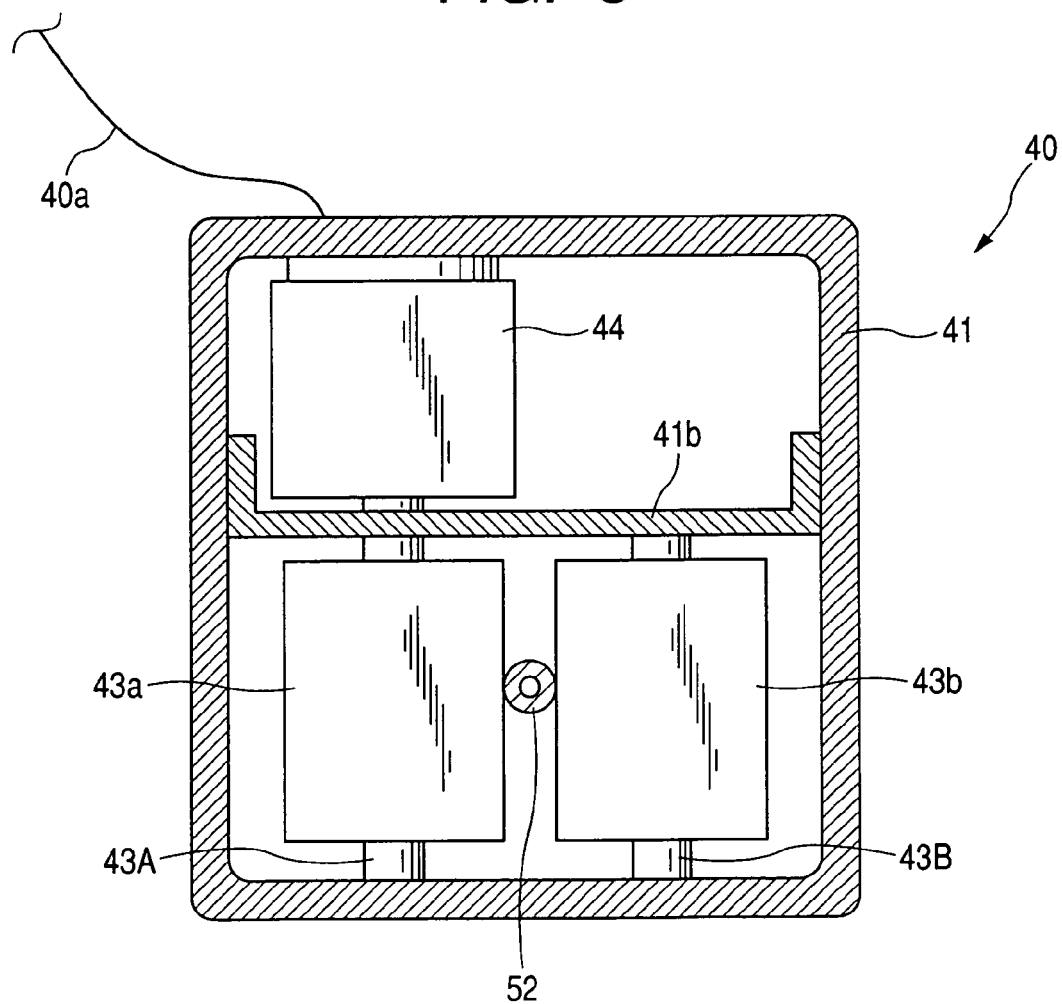
FIG. 8 is a laterally sectioned view of the instrument conveying unit.

Referring to FIGS. 7 and 8, the instrument conveying unit 40 will now be detailed.

As shown in FIG. 7, the instrument conveying unit 40 is provided with a box-shaped member 41 and two rollers 43a and 43b rotatably arranged within the box-shaped member 41. In one of the walls forming the box-shaped member 41, formed is an insertion hole portion 42 through which the sheath 52 of the therapeutic instrument 50 is inserted, while in the opposite wall to the wall with the insertion hole portion 42 formed, formed is a scope fixing member 41a. This scope fixing member 41a guides the sheath 52 into the therapeutic-instrument channel 11CH of the endoscope 10 and is used as a connection to the instrument inlet structure 12d of the endoscope 10. The insertion hole portion 42 also serves as a guide guiding the sheath 52 into the channel 11CH.

The insertion hole portion 42 is filled with a clamp plug 42a made from elastic material, in which the clamp plug 42a still has an insertion hole through which the sheath 52 is slidably inserted and pulled out. Meanwhile the scope fixing member 41a is linked with the opening of the therapeutic-instrument channel at the instrument inlet structure 12d in an airtight manner.

As a result, when the sheath 52 of the therapeutic instrument 50 is inserted or pulled out in a case where the body cavity is expanded by air supply or water supply via the endoscope 10 in order to facilitate an easy observation therein, the clamp plug 42a and scope fixing member 41a keep the air tightness of the therapeutic-instrument channel so as to prevent a drop in the pressure within the body cavity.

The two rollers 43a and 43b in the box-shaped member 41 are made from, for example, elastic material and rotatable by rotation shafts 43A and 43B, respectively. Both rollers 43a and 43b press, by their rotations, the outer surface of the sheath 52 of the therapeutic instrument 50, placed in a gap formed between the rollers 43a and 43b, so as to allow the sheath 50 to go forward and go back (that is, inserted and pulled out) through the therapeutic-instrument channel 11CH.

Of both rollers, one roller 43a is a driving roller and its rotation shaft 43A is driven by an electric motor 44 placed in the box-shaped member 41 (refer to FIGS. 7 and 8). Meanwhile the other roller 43b is a driven roller of which rotation helps the sheath 52 move smoothly which go forward and backward in to the rotation of the driving roller 43a.

The rollers 43a and 43b are rotatably supported from the side walls and a supporting plate 41b in the box-shaped member 41 such that the rollers 43a and 43b are spaced apart from each other to form the respective roller surfaces a gap of predetermined length therebetween and the respective rotation shafts 43A and 43B are in parallel to each other.

Figure 9:
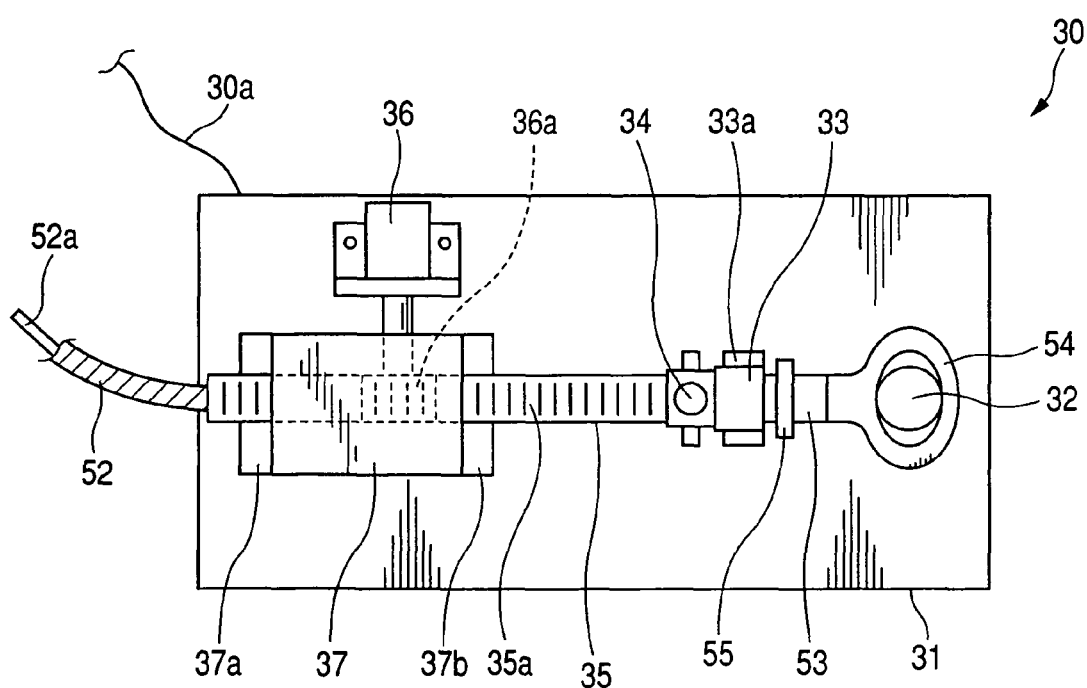
FIG. 9 is the plan view showing an instrument operating unit employed by the endoscope system.
Figure 10:
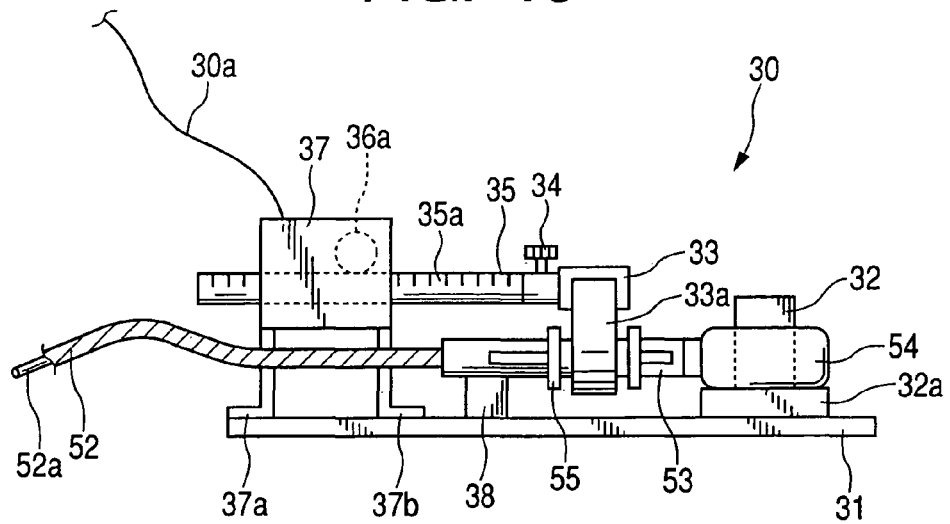
FIG. 10 is a side view of the instrument operating unit.
Figure 11:
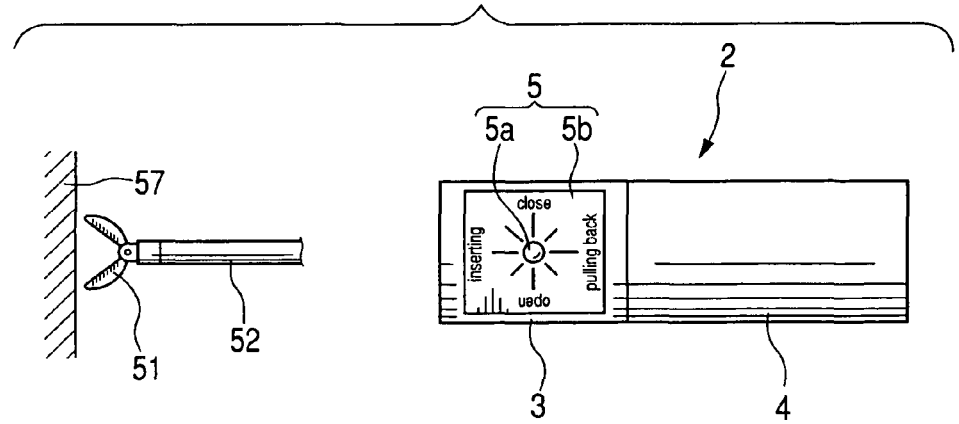
FIGS. 11 and 12 are illustrations each exemplifying how to manipulate an input device operating a biopsy forceps serving as a therapeutic instrument.

Referring to FIGS. 9 and 10, the instrument operating unit 30 will now be detailed.

As shown, the instrument operating unit 30 is provided with a plate-like base 31, a ring holding member 32 protruded from a surface of the base 31, a slider holding member 33 pinching a slider 55 of the therapeutic instrument 50, and other some components including a rack 35, a motor 36, a holding box 37, a mounting portion 38. Of these, the rack 35 is linked with the slider holding member 33 by a screw 34. The motor 36 has a rotation shaft on which a pinion gear 36a is secured so as to engage with a liner gear portion 35a of the rack 35. The holding box 37 is secured on the base 31 by securing members 37a and 37b and accommodates therein the pinion gear 36a, and holds the rack 35 to allow its linear motions for inserting and pulling-back operations. The mounting portion 38 is placed on the base 31 and supports the handle 53 of the therapeutic instrument 50.

The ring holding member 32 is mounted on an annular ring base 32a to be built thereon and arranged so as to be inserted into a finger-engaging ring 54 of the therapeutic instrument 50, so that the handle 53 is held at the instrument operating unit 30. The ring base 32a is fixedly mounted on the base at a position near to one end of the base 31.

The ring holding member 32 is shaped into a column having an outer diameter substantially equal to an inner diameter of the finger-engaging ring 54, thus securely holding the handle 53, that is, the therapeutic instrument 50. Incidentally the outer diameter of the ring holding member 32 may be formed to have a dimension slightly smaller than the inner diameter of the finger-engaging ring 54, if the ring holding member 32 is used with an elastic tube member mounted on the outer surface of the member 32. Employing this manner allows the handle 53 to be securely held by the instrument operating unit 30.

The ring base 32a has a predetermined height, whereby the handle 53 of the therapeutic instrument 50 is separated from the base 31 by a predetermined distance.

As shown in FIGS. 9 and 10, the slider holding member 33 is formed to have two holding plates 33a extending in an up-and-down direction perpendicular to the base 31, in which the holding members 33a hold the slider 55 of the therapeutic instrument 50 by pinching the slider 55 by the sides. Specifically, the slider 55 is formed into a drum-like shape having a flange on each of both axial end sides thereof, so the two holding members 33a are placed to pinch a body portion existing between the flanges. The slider holding member 33 is linked with one end of the rack 35 by a setscrew 34, as described before.

The pinion gear 36a, which can be rotated together with the rotation of the motor 36, is engaged with the linear gear portion 35a. Thus the rotation of the pinion gear 36a will cause the rack 35 to selectively move forward and backward in the axial (longitudinal) direction of the handle 53. This movement becomes relative motions to the holding box 37. Thus the slider holding member 33 allows the slider 55 to move along the handle 53 for inserting and pulling-out operations of the therapeutic instrument 50.

As described, the therapeutic instrument 50 has an operating wire 52a that passes through the bore of the sheath 52, and a distal end of the operating wire 52a is linked to the therapeutic member 51 and the other base end is linked to the slider 55. The sheath 52 and the operating wire 52a compose the tubular portion of the instrument 50. Conveying the sheath 52 results in conveying the operating wire 52a, together with the therapeutic member 51 disposed at the distal end thereof.

Thus, in response to the forward and backward motions of the sliders 55 in the axial direction of the handle 53, the operating wire 52a is pulled or relaxed so that these pulling and relaxation motions are converted to given operations of the therapeutic operations. In the present embodiment, the therapeutic member 50 is a biopsy forceps, so that the given motions are open and close operations of a gator-grip-shaped gripping portion thereof.

Figure 41:
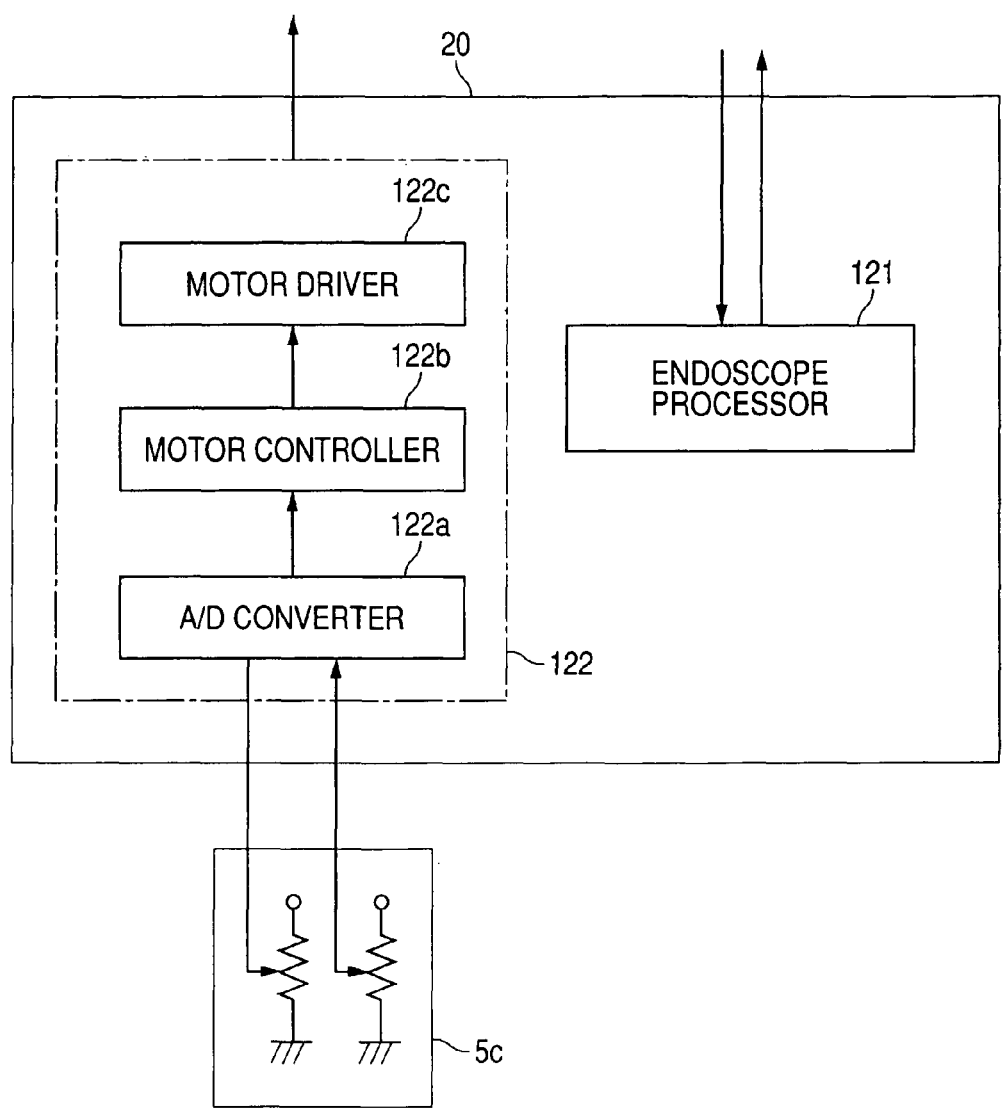
FIG. 41 is a functional block diagram showing a controller mounted in the endoscope system according to the first and third embodiment.

With reference to FIG. 41, the controller 20 will now be detailed.

As shown in FIG. 41, the controller 20 is configured to function as at least an endoscope processor 121 and a motor control unit 122. The motor control unit 122 is provided with an A/D converter 122a, a motor controller 122b, and a motor driver 122c.

As is known, the endoscope processor 121 is configured to perform processing necessary by the endoscope 10 itself. The processing includes processes for air supply, water supply, suction, illuminating, and imaging.

Meanwhile, in the motor control unit 122, the A/D converter 122a receives through the signal cable 2a two types of analogue signals generated by the processing circuit 5c of the input device 5 in response to tilt operations. The two types of analogue signals are for the motors 44 and 36 of both the units 40 and 30, respectively. Thus the A/D converter 122a converts the analog signals to corresponding digital signals, before transmitting them to the motor controller 122b. This motor controller 122b is configured to control the operations of the motor driver 122c so that both motors 44 and 36 are driven by drive signals which depend on the tilt operations at the input device 5.

That is, the tilt directions of the operation lever 5a (refer to FIG. 4) are reflected in the rotating directions of both motors 44 and 36 in a controlled manner.

In addition, since an amount of tilt of the operation lever 5a is detected by the processing circuit 5c, with the result that the motor controller 122b controls the motor driver 122c so as to the tilt amount is reflected in rotation speeds of the motors 44 and 36. The drive commands to both motors 44 and 36 are set such that the deeper the tilted angle of the operation lever 5a from a perpendicular position thereof, the larger the rotational speeds of the motors 44 and 36.

Figure 42:
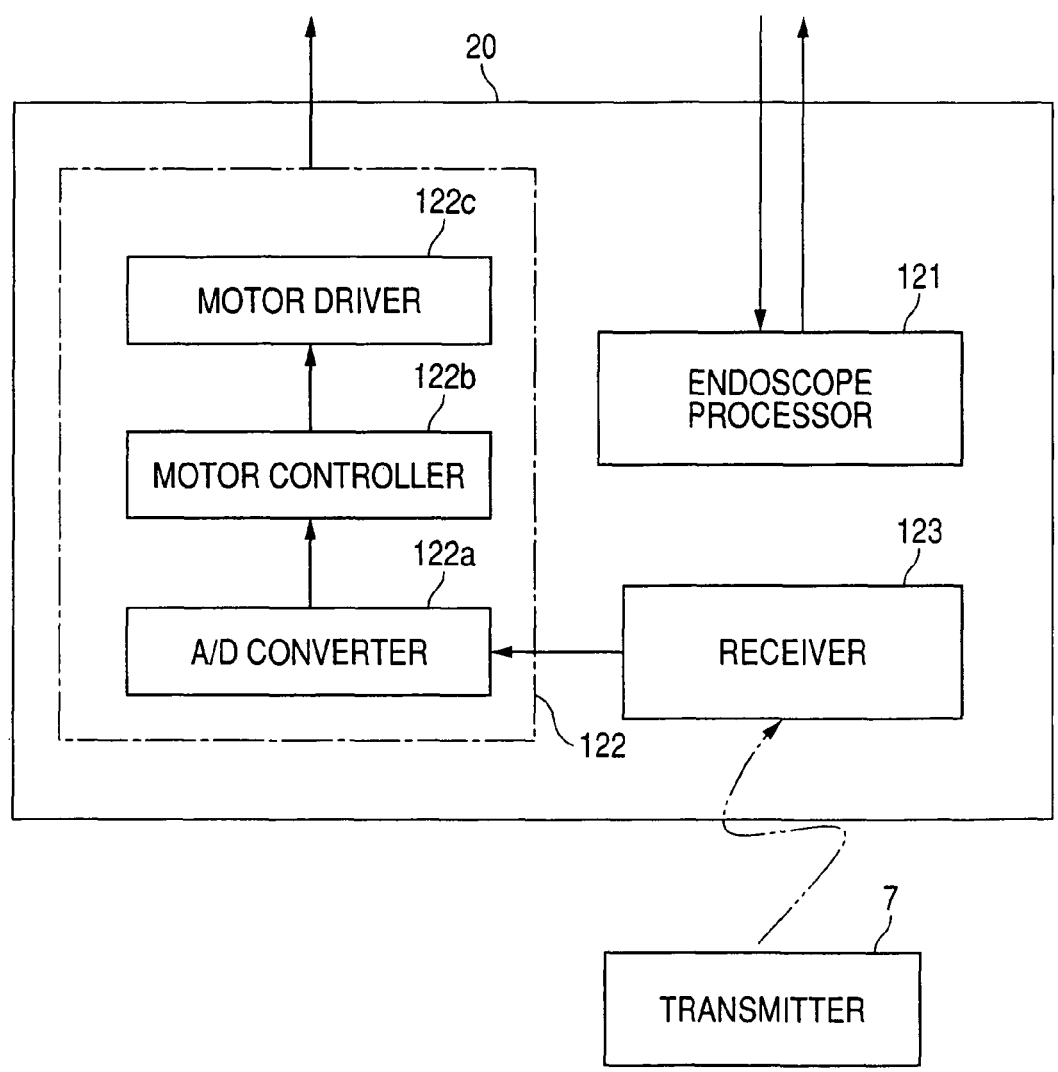
FIG. 42 is a functional block diagram showing a controller mounted in the endoscope system according to the second embodiment.

Incidentally, in cases where as shown in FIG. 6 the manipulating unit 2 is formed into a wireless type, the controller 20 may be formed as shown in FIG. 42, where a receiver 123 is provided in addition to the foregoing endoscope processor 121 and motor control unit 122.

The receiver 123 is formed to receive signals from the transmitter 6 provided in the manipulating unit 6, in which the signals include information indicative of both of a direction along which the operation lever 5a is tilted and a tilted angle of the operating lever 5a. The receiver 123 is configured to output such signals to the motor control unit 122. As a result, in the same way as the wired configuration, the motor control unit 122 is able to control the rotation directions and speeds of both motors 44 and 36 of the instrument conveying and operating units 40 and 30, respectively.

The operations and advantages of the endoscope system 1 according to the present embodiment will now be described.

An operator (doctor) examines a body cavity of an object being examined with monitoring acquired endoscope images, during which time when a lesion is found in the cavity, the operator is able to treat the lesion by performing various therapeutic operations such as ablation. In the present embodiment, use of the biopsy forceps will now be exemplified.

In this case, as illustrated in FIG. 9, the handle 53 of the therapeutic instrument 50 is fixed at the instrument operating unit 30. Concretely, the operator the slider holding member 33 with the rack 35 removed is loaded on the slider 55 so as to put the ring holding member 32 in the finger-engaging ring 54 of the handle 53.

In this operation, the operator inserts the ring holding member 32 into the finger-engaging ring 54 until the handle 53 of the therapeutic instrument 50 partly touches the mounting portion 38 on the base 31. Further, as shown in FIG. 10, the operator uses the setscrew 34 to connect the slider holding member 33 and the rack 35 with each other.

The operator then proceeds to loading the instrument conveying unit 40 to the instrument inlet structure 12d of the endoscope 10. Through the unit 40, the sheath 52 of the therapeutic instrument 50 is inserted into the therapeutic-instrument channel 11CH of the endoscope 10 so that the therapeutic member 51 advances therein at the head. In this work, the operator continues the insertion until the therapeutic member 51 passes the two rollers 43a and 43b in the instrument conveying unit 40 to allow the sheath 52 to begin being pressed between the two rollers 43a and 43b. Alternatively, the operator may manually carry out an initial insertion, in which the sheath 52 is continued to be inserted into the therapeutic-instrument channel until the therapeutic member 51 reaches the distal end of the insertion tube 11 (i.e., the therapeutic-instrument channel).

With observing endoscopic images, the operator then inserts the insertion tube 11 into a body cavity of an object so that the distal section 11a is inserted at the head in the cavity. In this operation, according to need, the operator further inserts the insertion tube 11 and bends the bendable section 11b such that the distal section 11a positions near the lesion concerned and adjusts its position to allow the endoscopic view to catch the lesion. Then the operator performs therapeutic operations toward the lesion with the help of the endoscopic images.

Specifically, as shown in FIG. 2, the operator is able to make a one-handed grasp of the manipulating unit 2.

And, by making the operation lever 5a of the manipulating unit 5 in a desired direction, the therapeutic instrument 50 can be subjected to open/close operations of its therapeutic member 51 and conveying (i.e., inserting and pulling-back) operations of the sheath 52 (together with the operation wire 52a).

To be specific, when the operator tilts the operation lever 5a in the direction indicted by the marking "inserting" on the lever support 5b (refer to FIGS. 11 and 12), the sheath 52 (together with the operating wire 52a) of the therapeutic instrument 50 can be made to advance forward (i.e., inserted). In contrast, when the operator tilts the operation lever 5a in the direction indicted by the marking "pulling back," the sheath 52 (together with the operating wire 52a) of the therapeutic instrument 50 can be made to go back (i.e., pulled back).

Further, if the operator makes the operation lever 5a tilt in the direction indicated by the marking "open" or "close," the therapeutic member 51 can be opened or closed in a selective manner.

That is, in response to an operator's tilt operation toward the forward or backward direction (i.e., a direction indicated by the marking "inserting" or "pulling back"), information showing the tilt of the operation lever 5a is sent out as a corresponding analogue signal from the processing circuit 5c to the controller 20 via the signal cable 2a. In the controller 20, the analogue signal is digitized and fed to the motor controller 122b, which controls the motor driver 122c. Under the control of the motor controller 122b, the motor driver 122c drives, via the electric cable 40a, the motor 44 (refer to FIG. 8) of the instrument conveying unit 40 such that both of the rotational direction and the rotational speed of the motor 44 are set to specified ones. The motor 44 is also powered through the electric cable 40a. Responsively to the rotation of the motor 44, the driving roller 43a in the instrument conveying unit 40 is rotated in a specified rotation direction, which causes the sheath 52 (pressed between the tow rollers 43a and 43b) to selectively move forward or backward through the therapeutic-instrument channel 11CH of the endoscope 10.

Hence, by selectively making the operation lever 5a tilt in the forward or backward, the therapeutic member 51 can be moved forward or backward, that is, can emerge or submerge from or in the distal section 11a of the insertion tube 11 of the endoscope 10.

That is, in response to an operator's tilt operation toward the rightward or leftward direction (i.e., a direction indicated by the marking "close" or "open"), information showing the tilt of the operation lever 5a is sent out as a corresponding analogue signal from the processing circuit 5c to the controller 20 via the signal cable 45a. In the controller 20, the analogue signal is digitized and fed to the motor controller 122b, which controls the motor driver 122c. Under the control of the motor controller 122b, the motor driver 122c drives, via the electric cable 30a, the motor 36 (refer to FIGS. 9 and 10) of the instrument operating unit 30 such that both of the rotational direction and the rotational speed of the motor 36 are set to specified ones. The motor 36 is also powered through the electric cable 30a.

Responsively to the rotation of the motor 36, the pinion gear 36a is rotated, which causes the linear gear portion 35a to move the rack 37 linearly relatively to the holding box 37. The slider holding member 33, which is linked with the rack 35, moves the slider 55 of the therapeutic instrument 50 forward or backward along the axial direction of the handle 53 in a selectively manner, whereby the instrument 50 is subjected to traction or relaxation in a controlled manner.

Hence, by selectively making the operation lever 5a tilt in the rightward or leftward, the therapeutic member 51 can be opened or closed.

In addition when the operator tilts the operation lever 5a toward any of four regions sectioned among the four tilt-direction markings "inserting," "pulling out," "open," and "close," the inserting or pulling-out operation can be done in parallel with the open or close operation in any combination.

Figure 12:
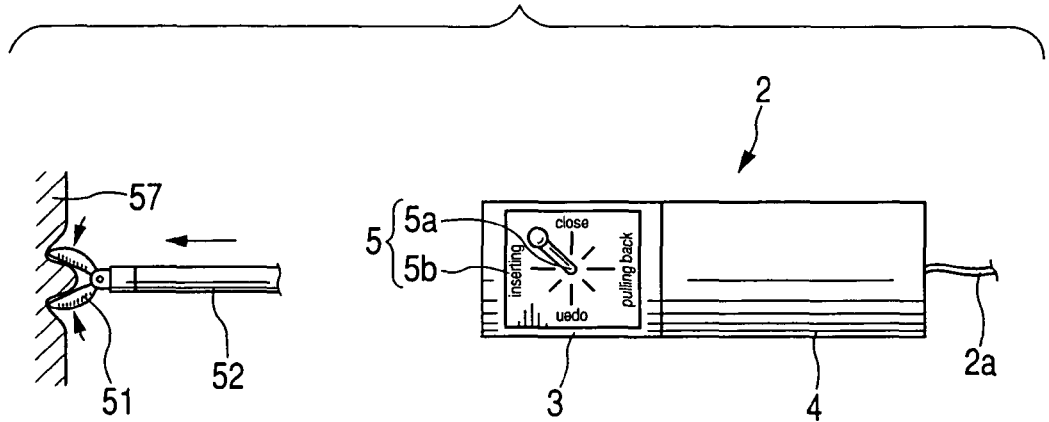

For example, in a state where the therapeutic member 51 of the therapeutic instrument 50 reaches a tissue 57, the operator tilts the operation lever 5a of the manipulating unit 2 into a tilt-direction range between the markings "inserting" and "close," as shown in FIG. 12. This operation allows the therapeutic member 51 to go forward the tissue 57 and to be closed concurrently with the forward motion. Hence, as shown in FIG. 12, it is possible to make the member 51 gather the tissue 57. The other combined operations can also be carried out in the same manner as the above.

Further, depending on a tilted angle of the operation lever 5a, the speed of the inserting or pulling-out operation of the sheath 52 and/or the speed of the open or close operation of the therapeutic member 51 can be controlled respectively.

The tilted angle is measured from the initial position (perpendicular position) of the operation lever 5a.

By the way, the therapeutic instrument 50 combined with the endoscope 1 will no be limited to the biopsy forceps, but may employ various therapeutic members such as a high-frequency surgical snare, a cannulation tube, and a basket grasping forceps, which are described below.

In the endoscope system 1 according to the present embodiment, it is possible to remarkably improve the operationality of the therapeutic techniques for operating the therapeutic member 51 that requires the advancement of the sheath 52. The therapeutic techniques will now be exemplified as to a high-frequency surgical snare, a cannulation tube, and a basket grasping forceps.

First Therapeutic Technique

Figure 13:
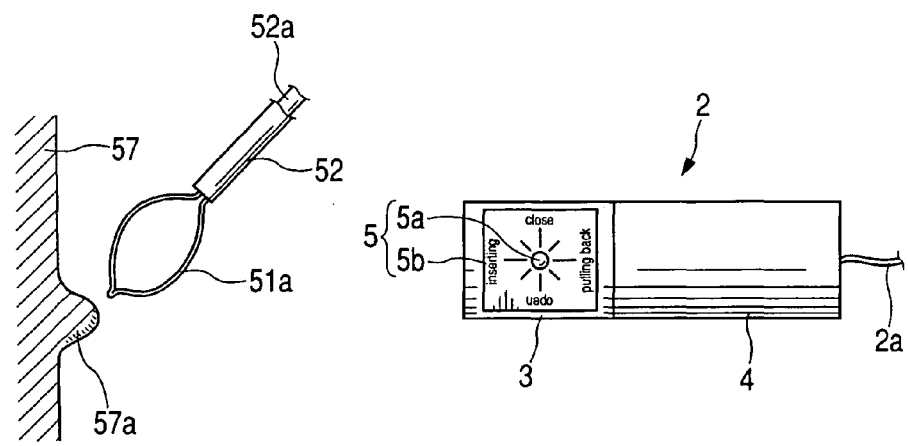
FIGS. 13 and 14 are illustrations each exemplifying how to manipulate the input device operating a high-frequency surgical snare serving as the therapeutic instrument.
Figure 14:
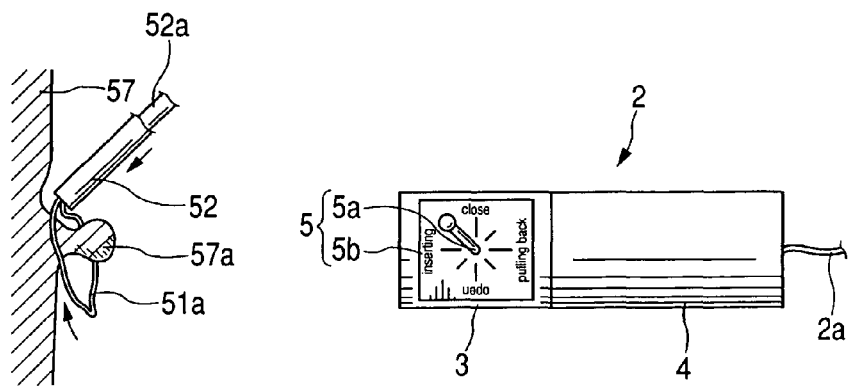

As shown in FIGS. 13 and 14, when the high-frequency surgical snare is employed as the therapeutic instrument 50, an operator is able to remove lesions such as a polyp in tissue or stomach wall on the following procedures. First of all, an operator conforms on endoscopic images the presence of a lesion 57a, such as a polyp, to be treated of tissue 57, as shown in FIG. 13. Then the operator engages in moving forward the sheath 52 of the instrument 50 toward the tissue 57, during the operation of which a loop wire 51a, that is, the therapeutic member, is tried to hook on the lesion 57a, and then the loop wire 51a is pulled back into the sheath 52.

As described before, the high-frequency surgical snare 50 has the handle 53 arranged at the base end thereof, in which sliding the slider 55 along the handle 53 allows the loop wire 51a to submerged into the sheath 52 and emerge from the distal end of the sheath 52.

Use of the high-frequency surgical snare 50 will now be explained again in a fourth embodiment, in which supplying high-frequency current to the loop wire 51a makes it possible to cut living tissue and coagulate blood vessels. A high-frequency electric code is connected to the metal-made operating wire 52a in the sheath 52 via the slider 55, thus realizing an electrical connection with the loop wire 51a. From the slider 55, the high-frequency electric code extends to a not-shown high-frequency power supply.

Conventionally, it has been difficult for one operator to manually insert and pull back the sheath 52 in a state the operator himself or herself operates the loop wire 51a concurrently with such conveying operations. Thus, the conveying operations of the sheath 52 and the therapeutic operations of the loop wire 51a result in team work, which has still confronted with difficulties to conduct good communication among the team members.

Figure 15:
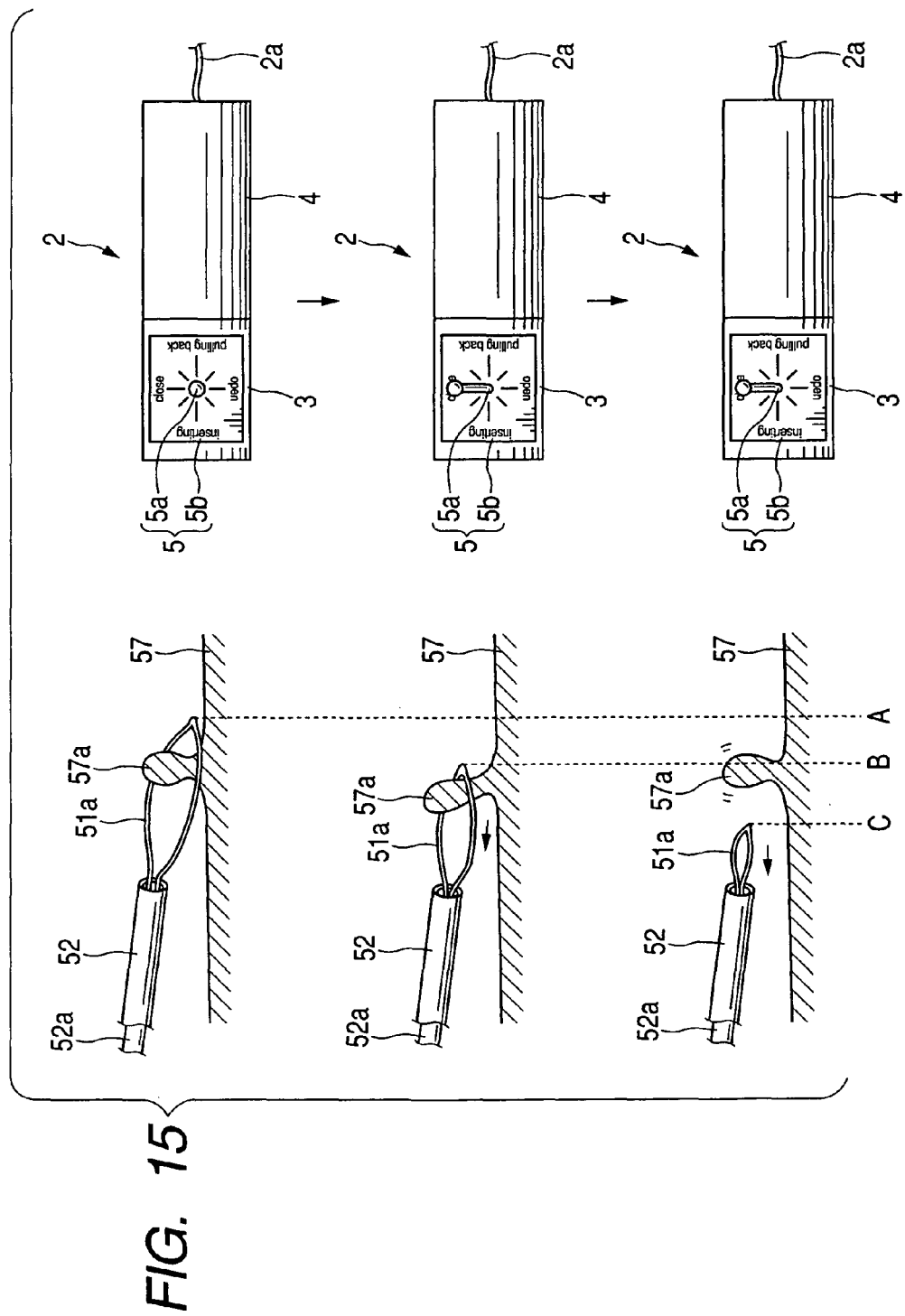
FIG. 15 is an illustration explaining a difficulty confronted by a conventional therapeutic technique when the high-frequency surgical snare is used.

The difficulties in the conventional operations are illustrated in FIG. 15. As shown, when the loop wire 51a is made to shrink from a state where the loop wire 51a is hooked on the lesion 57a on the tissue 57 in a body cavity, the loop wire 51a is accommodated into the sheath 52 without changing the position of sheath 52.

It is thus difficult to allow the loop wire, 51a to catch the lesion well, because the loop wire 51a is likely to drop off from the region 57a. This is mainly due to the unchanged position of the sheath 52, as illustrated in FIG. 15. Because of the unchanged position, a state where the loop wire 51a is hooked on the lesion 57a (shown by a dotted line "A") changes to a state in which the head of the loop wire 51a is shown by a dotted line "B," and than to a state that of the loop wire 51a is shown by a dotted line "C," if the loop wire 51a is desired to be accommodate into the sheath 52. Thus, as the loop wire 51a is reduced in its radius, the hooked loop wire 51a is likely to drop off from the lesion 57a.

However, in the present example, the high-frequency surgical snare 50 is equipped with the handle 53 to be arranged in the instrument operating unit 30, so that an operator himself or herself operates to not only convey (insert or pull back) the sheath 52 but also therapeutically operate the loop wire 51a in parallel with each other.

To be specific, an operator operate the operation lever 5a of the manipulating unit 2 such that the lever 5a is tiled into an intermediate region sectioned by the tilt-direction markings "inserting" and "close", as shown in FIG. 14, from the neural position shown in FIG. 13. Responsively to this tilt operation, the sheath 42 advances, during which time the loop wire 51a is reduced in its diameter (shrunk) and pulled into the sheath 52. Hence, an operator is able to easily reduce the diameter of the loop wire 47a with the loop wire 51a still hooked on the lesion 47a, thereby ensuring that the lesion 57a is removed steadily.

Figure 16:
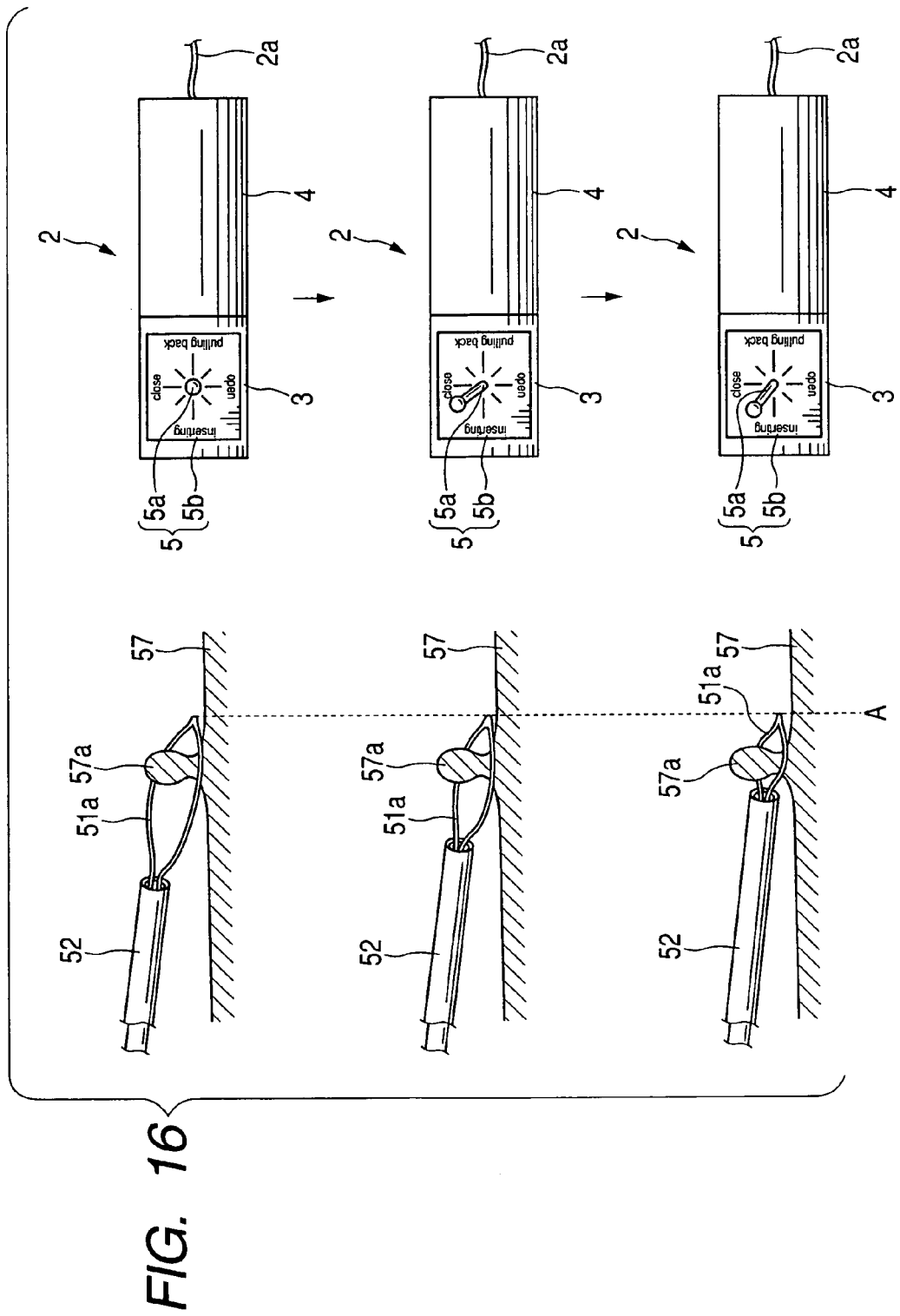
FIG. 16 is an illustration explaining how to manipulate the high-frequency surgical snare based on the therapeutic technique using in input device according to the present invention.

That is, as shown in FIG. 16, tilting the operation lever 5a toward the intermediate angular range between the tilt-direction markings "insert" and "close," the sheath 52 is made to advance and concurrently with this, the loop wire 51a is subjected to shrinkage to be accommodate into the sheath 52. The advancement of the sheath 52 makes up of a positional pullback of the loop wire 51a (refer to a dotted line "A"), still keeping the head of the loop wire 51a at the almost same position. Thanks to the fact that the loop wire 51a shrinks with being hooked on the lesion 57a, the lesion 57a can be removed easily and steadily.

Further, the operation lever 5a can be tilted toward any of the four intermediate angular ranges sectioned by the four tilt-direction markings, for operator's desired therapeutic operations of the therapeutic instrument 50.

Second Therapeutic Technique

A second therapeutic technique will now be explained by using a side-view type of endoscope used for the duodena, for instance. That is, the endoscope according to the present invention may be applied to such side-view type of endoscopes, not limited to the direct-view type of endoscope 10 explained in the first embodiment. In the present example, for the sake of a simplified explanation, the reference numerals attached to the endoscope 10 will also be applied to the side-view type of endoscope according this example.

Figure 17:
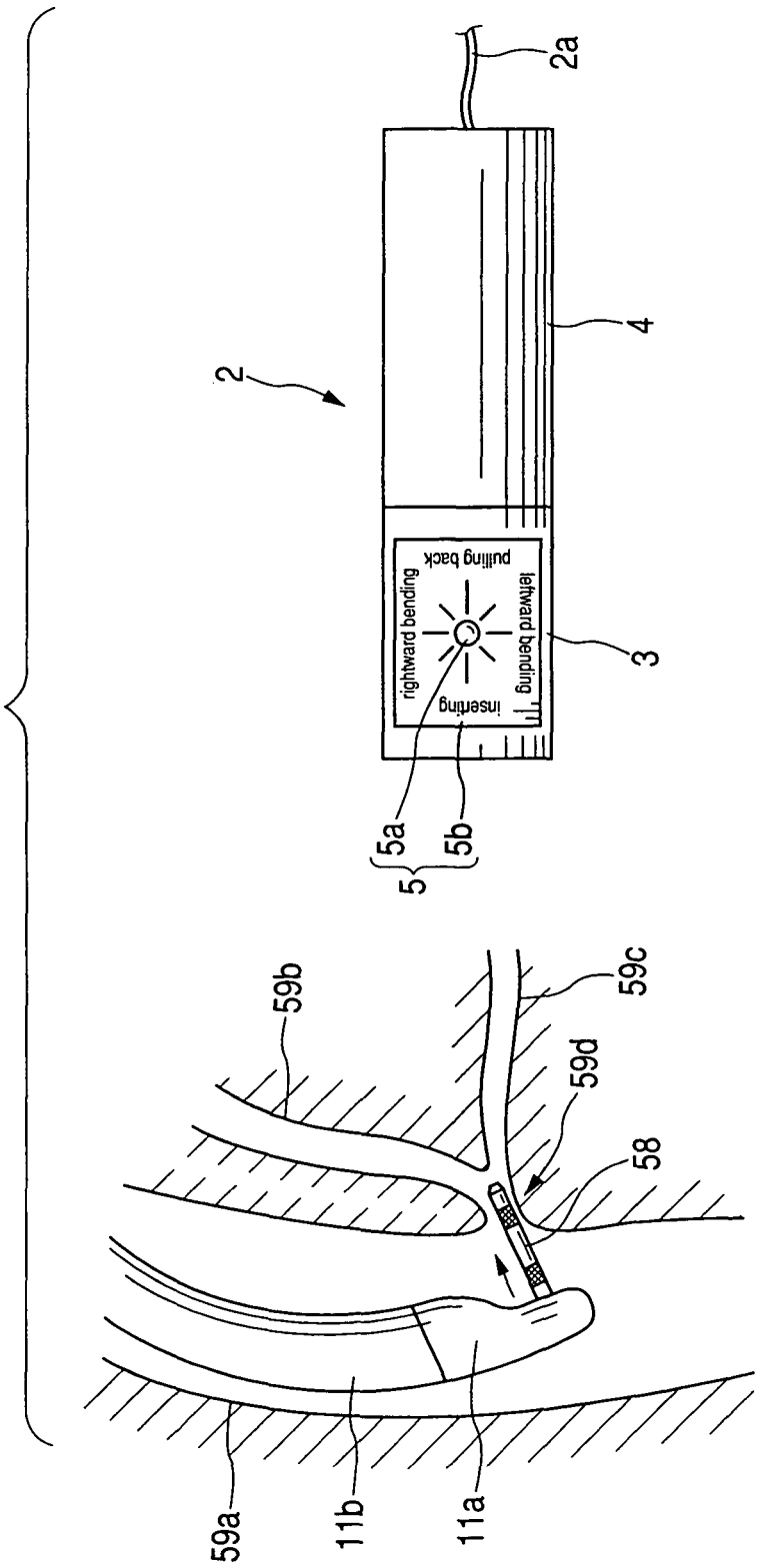
FIGS. 17 and 18 are illustrations each exemplifying how to manipulate an input device operating a cannulation tube serving as the therapeutic instrument.
Figure 18:
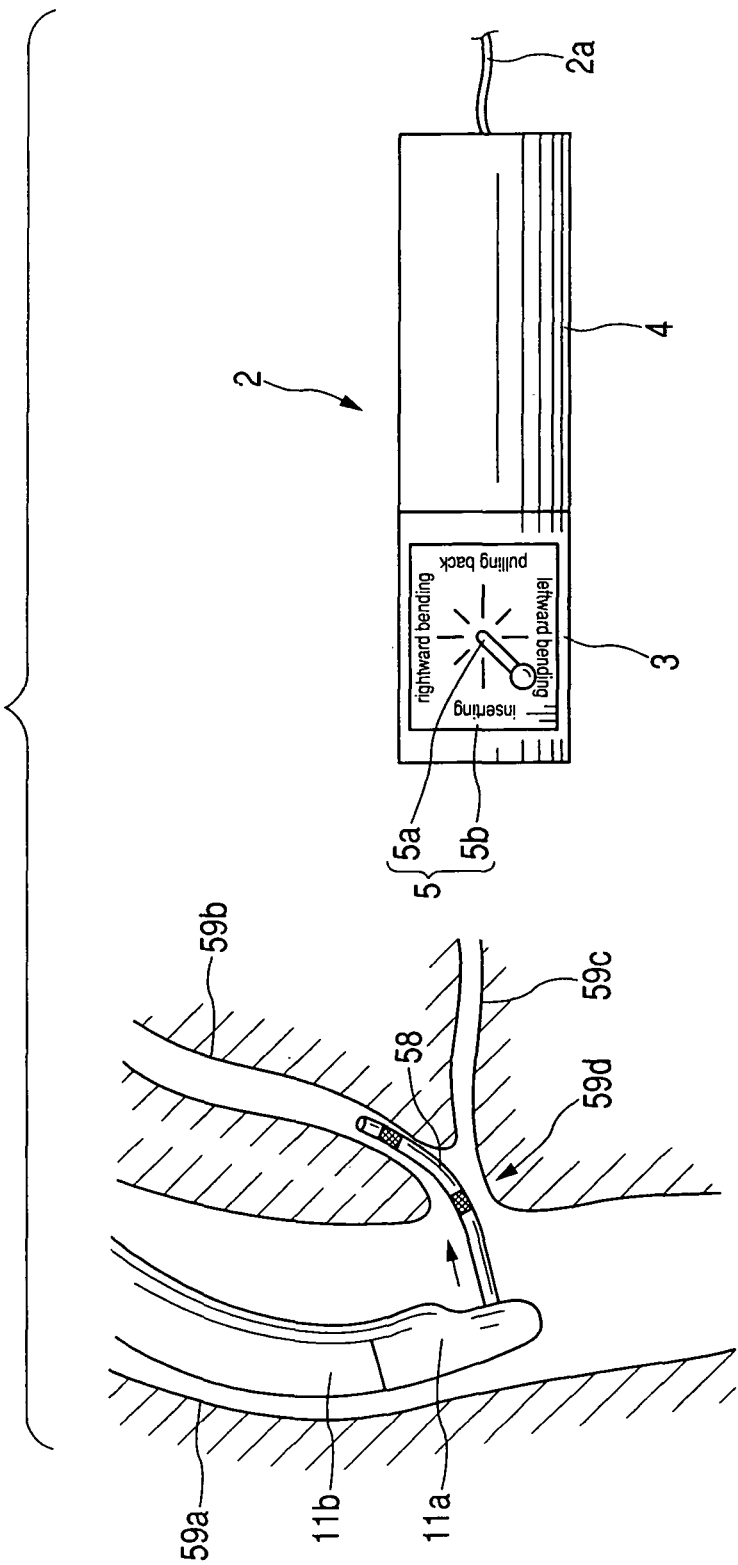

With reference to FIGS. 17 and 18, a cannulation tube 58, which serves as the therapeutic instrument, will now be exemplified. The cannulatin tube 58 is used to find the position and type of calculus in a bile duct 59b and functional abnormalities of a biliary tract. For such purposes, the cannulation tube 58 is inserted through a duodena 59a by using the insertion tube 11 of the endoscope 10 and used to inject a contrast agent into the bile duct 59b and a pancreatic duct 59c for endoscopic retrograde cholangio pancreatography (ERCP) and other therapy.

The cannulation tube 58 is linked with the foregoing handle 53 at the base end, so the slider 55 is slid along the longitudinal axis direction of the handle 53 to bend the distal end of the tube into two ways. The handle 53 is set to the instrument operating unit 30, whereby this cannulation tube 58 also is subjected to bending operations by responding to commands from the manipulating unit 2. For those operations, the manipulating unit 2 shown in FIG. 5 is employed for "inserting," "pulling back," "upward bending," and "downward bending" operations.

As shown in FIG. 17, an operator first operates the insertion tube 11 of the endoscope (side view type) 10 such that the distal section 11a is located in the vicinity of a papillary edge 59d of the duodena 59a, before tilts the operation lever 5a of the manipulating unit 2 toward the tilt-direction marking "inserting." By this tilt operation, the cannulation tube 58 emerges from a one-side window of the distal section 11a and is guided into the papillary edge 59d.

And, to insert the cannulation tube 58 into the bile duct 59b branching upward rather than the pancreatic duct 59e from the papillary edge 59d, the operation lever 5a is rotated toward the tilt-direction marking "upward bending" as shown in FIG. 18, with the operation lever 5a still tilted in the marking "inserting."

Responsively to these operations, the cannulation tube 58 passes the papillary edge 59d, and then is inserted into the bile duct 59b smoothly. In this way, the distal end portion of the cannulation tube 58 can be inserted into the bile duct 59b and bent along the bent direction of the bile duct 59b.

In addition, in the present endoscope system 1, the operation lever 5a can be adjusted to a desired tilt angle to change the inserting/pulling-back speed and the bent angle of the cannulation tube 58. This is helpful for facilitating subtle inserting operations of the cannulation tube 58.

Third Therapeutic Technique

Figure 19:
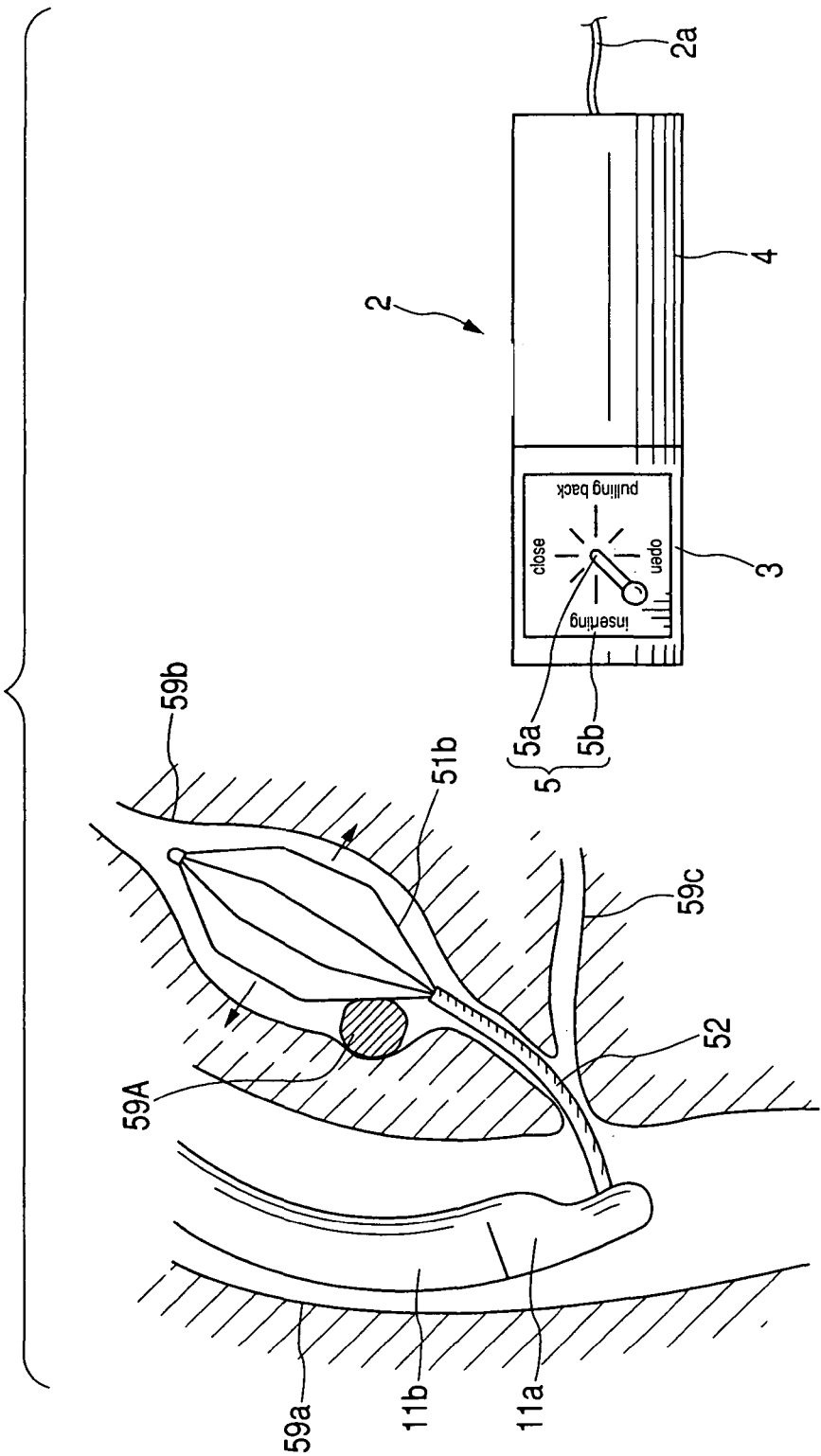
FIGS. 19 and 20 are illustrations each exemplifying how to manipulate an input device operating a basket grasping forceps serving as the therapeutic instrument.
Figure 20:
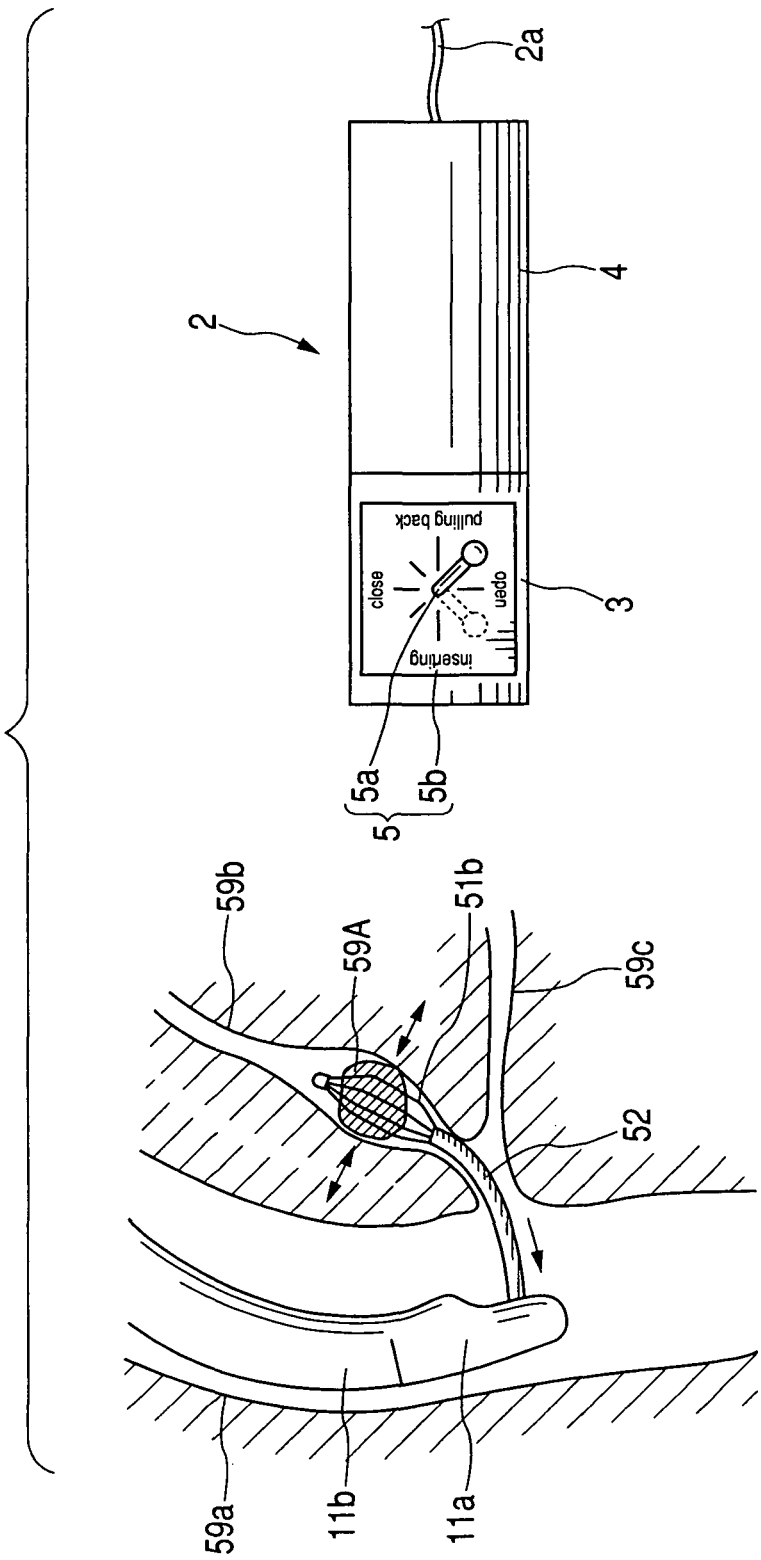

As shown in FIGS. 19 and 20, a third therapeutic technique relates to removal of calculus 59A from the bile duct 59b by using a basket grasping forceps 50 serving as the therapeutic instrument, when the calculus 59A is found by for example the endoscopic retrograde cholangio pancreatography.

As shown in FIG. 19, for operating the basket grasping forceps 50, the sheath 52 can be inserted into the bile duct 59b and a basket 51b of the forceps 50, serving as the therapeutic member, can be expanded in the duct 59b. For these two kinds of operations, an operator operates the operation lever 5a such that the lever 5a is tilted toward the marking "inserting" to insert the sheath 52 into the bile duct 59b and then tilted toward the marking "open" to allow the basket 51b to be emerged from the sheath 52 and developed near the calculus 59A in the bile duct 59b. In this case, the operation for inserting the sheath 52 and the operations for emerging and developing the basket 51b are not always necessary to be done simultaneously or in parallel with each other, and may be done sequentially. In this example, the manipulating unit 2 shown in FIG. 4 is used, which provides the markings "inserting," "pulling back," "open," and "close."

Then, as shown in FIG. 20, the operator tilts the operation lever 5a toward the tilt-direction regions between the markings "pulling back" and "close" and between the markings "pulling back" and "open" in turns for expanding and contracting the basket 51b. These operations make intervals between basket wires larger and smaller in turns and also change touching directions of basket wires to the calculus 59A, whereby the calculus 59A can be taken into the basket 51b. When this taking-in operation is completed, the operator tilts the operation lever 5a toward the tilt-direction range between the markings "pulling back" and "close," resulting in that the basket 51b is contracted, but still holding the calculus 59A therein, and pulled back from the bile duct 59b.

Accordingly, the endoscope 1 of the present embodiment can be used in combination with the basket grasping forceps 50 (therapeutic instrument) for removing foreign matters from body cavities. The basket 51b, that is, the therapeutic member of the forceps 50, is manipulated sensitively to make the basket 51b emerge from and submerge in the sheath 52 and, after this operation or in parallel with this operation, expand and contract with ease.

As described, in the endoscope system 1 of the present embodiment, an operator is able to manually operate the manipulating unit 2, which is at hand, for manipulating the therapeutic instrument 50 (including the cannulation tube 58) combined with the endoscope 10, without grasping the handle 53. Accordingly, the operator can manipulate the cannulation tube 58 by oneself when its sensitive operations are required, leading to steady operations of the instrument.

Second Embodiment

With reference to FIGS. 21-24, a second embodiment of the present invention will now to described. In the present embodiment, the similar or identical components to those in the first embodiment will be given the same reference numerals for a simplified explanation thereof. This manner of description will be true of the description of the succeeding embodiment and modifications.

In this embodiment, the medical instrument 50 is described as a basket grasping forceps as one example of the medical instruments. Alternatively the other instruments such as a biopsy forceps, high-frequency snare, and so on will be accepted by this endoscopic system. And the endoscope in this embodiment is of a side view type which is of the same type in the first embodiment.

Figure 21:
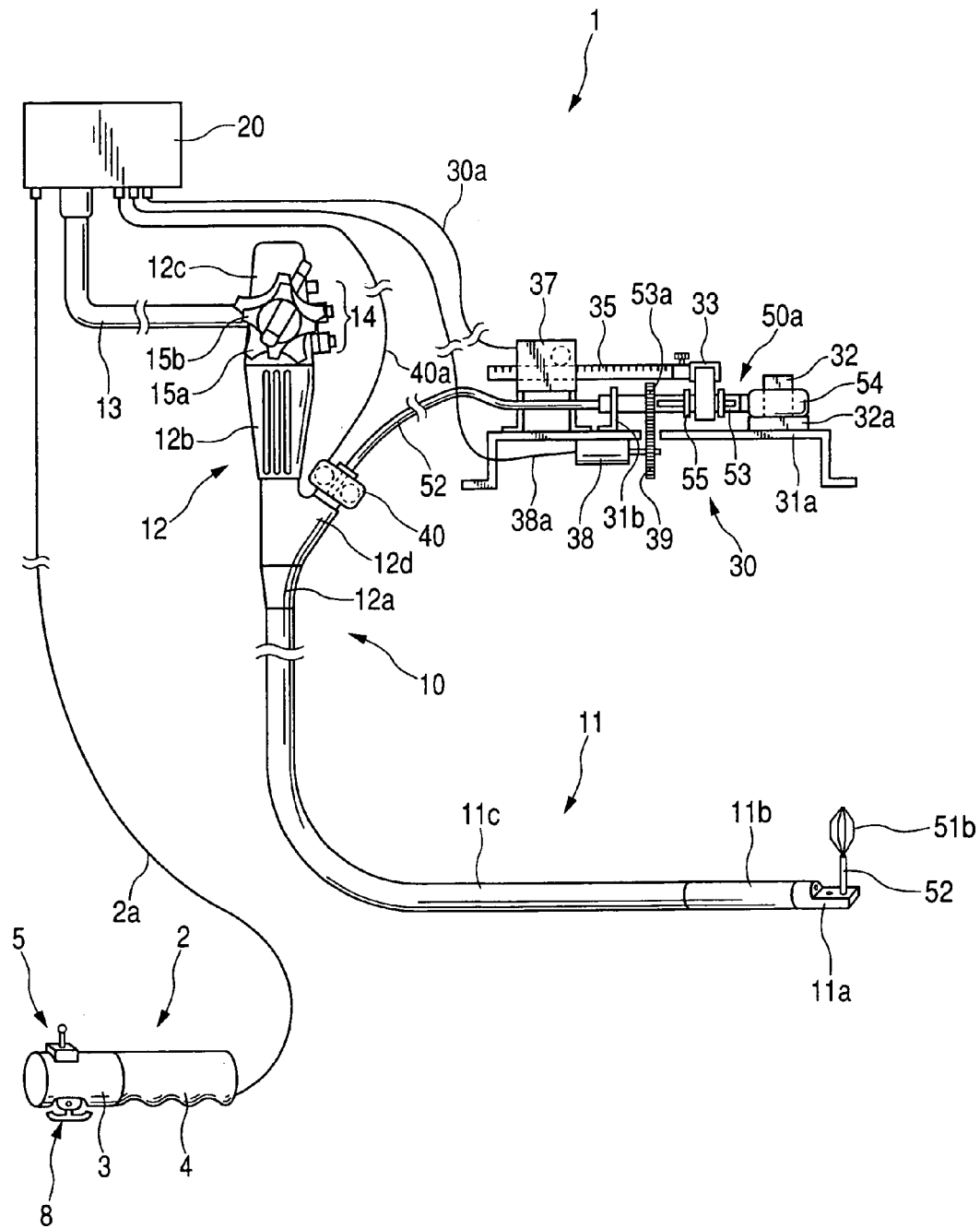
FIG. 21 is a schematic view showing the configuration of a main part of an endoscope system according to a second embodiment of the present invention.

As shown in FIG. 21, in the endoscopic system 1, the therapeutic member 51 of the therapeutic instrument 50 is freely rotatable about the longitudinal axis of the sheath 52 of the instrument with accompanying the rotation of the sheath 52. A biopsy forceps is one of the examples of such instruments. Specifically, the instrument operating unit 30 is provided with an electric motor 38 which gives the rotary force to the part of the sheath 52 near the end of the handling portion and permits the sheath 52 to be rotated.

Figure 22:
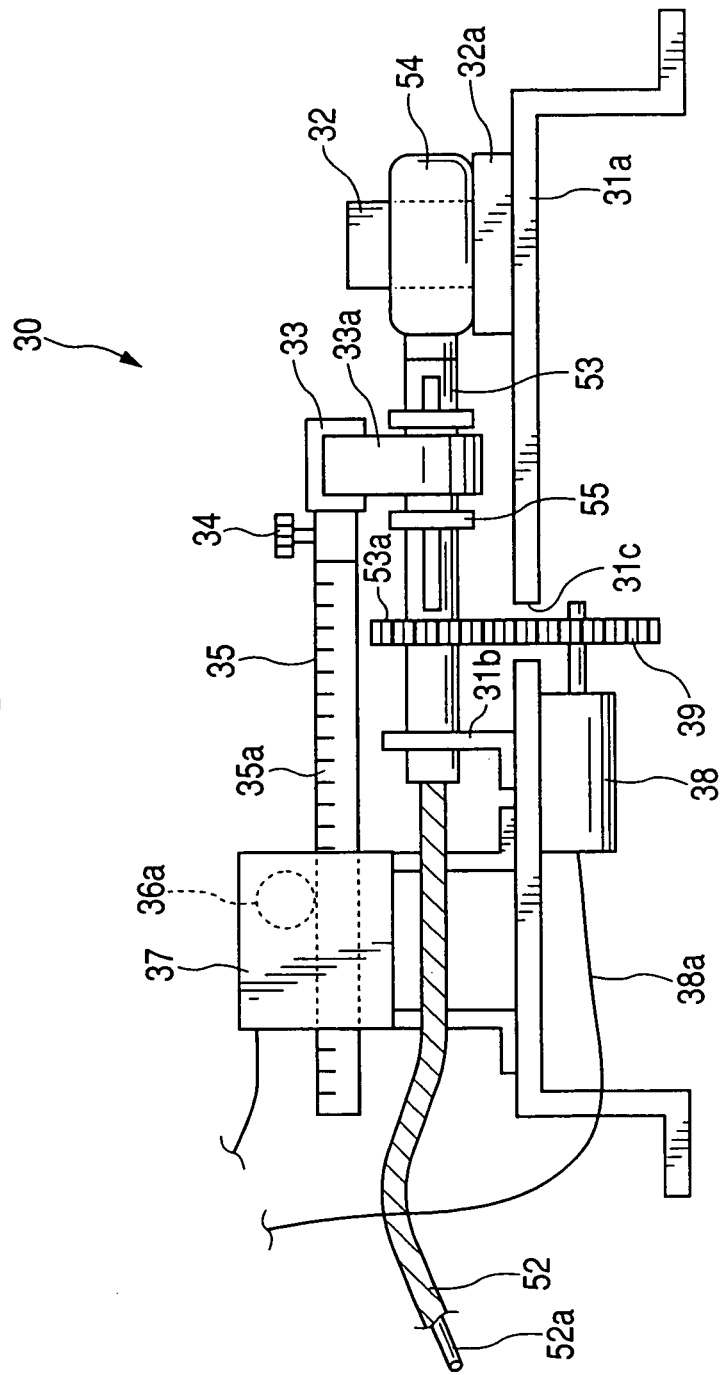
FIG. 22 is a side view showing an instrument operating unit adopted by the endoscope system of the second embodiment.

This electric motor 38 is provided with a rotation transferring gear (simply referred to as a gear) 39, and is electrically connected to the controller 20 via an electric cable 38a. This motor 38 is, as shown in FIG. 22, mounted on the rear side of the base body 31a of the instrument operating unit 30 which is roughly the same shape as a hat.

In the base body 31a is formed a hole 31c so as to be enable a direct view toward the gear 39 of the electric motor 38 from the upper side of the base body on which the handling portion 53 of the instrument 50 is placed. Furthermore, the base body 31 is equipped with the supporting portion 31b for rotatably supporting the handling portion 53.

On the end of the handling portion 53 of the instrument 50, a passive gear (simply referred to as a gear) 53a is placed, and is engaged with the gear 39 which is come out from the surface of the base body 31a through the hole 31c.

Figure 23:
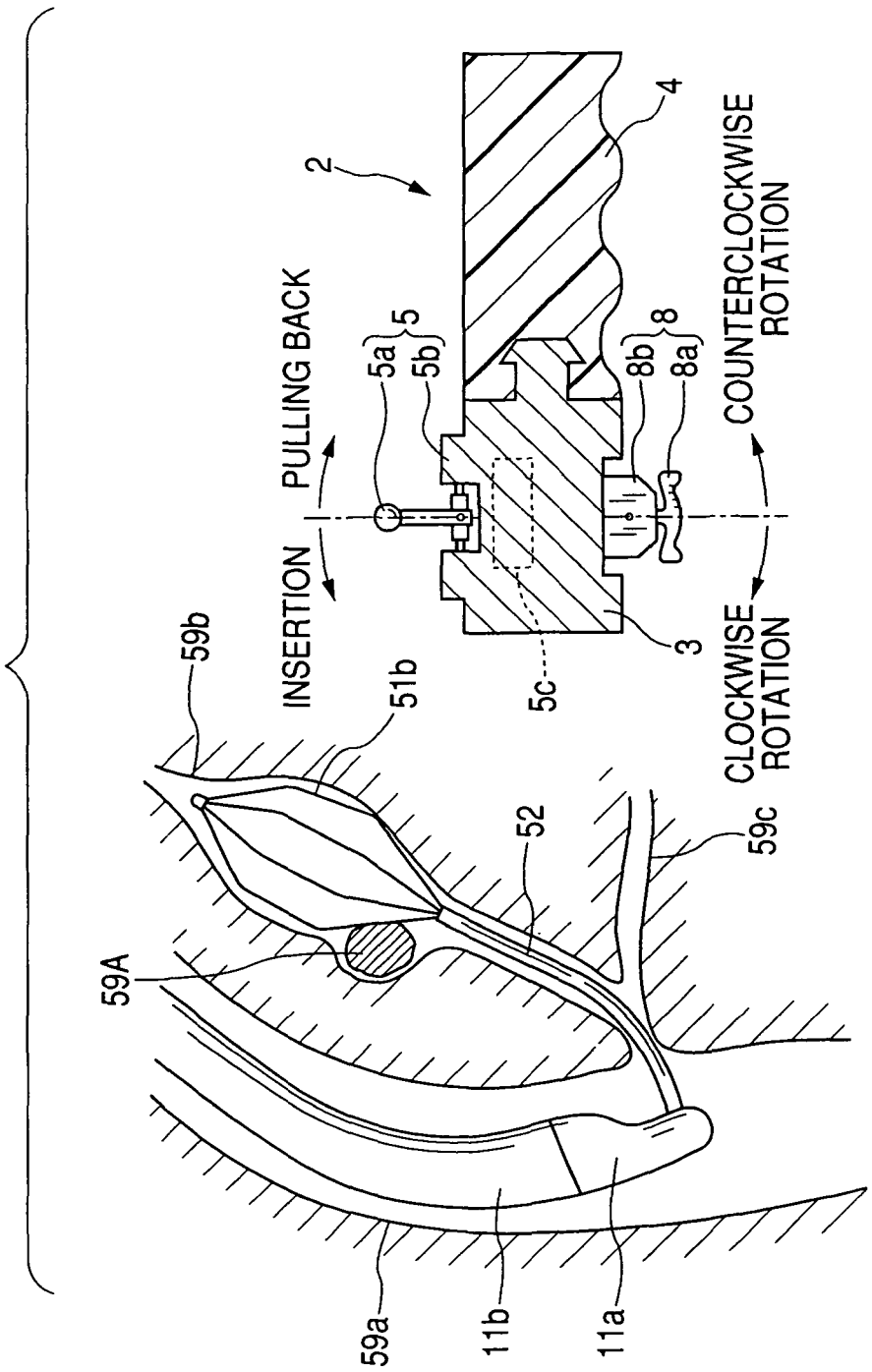
FIGS. 23 and 24 are illustrations each exemplifying how to manipulate an input device operating a basket grasping forceps serving as the therapeutic instrument.
Figure 24:
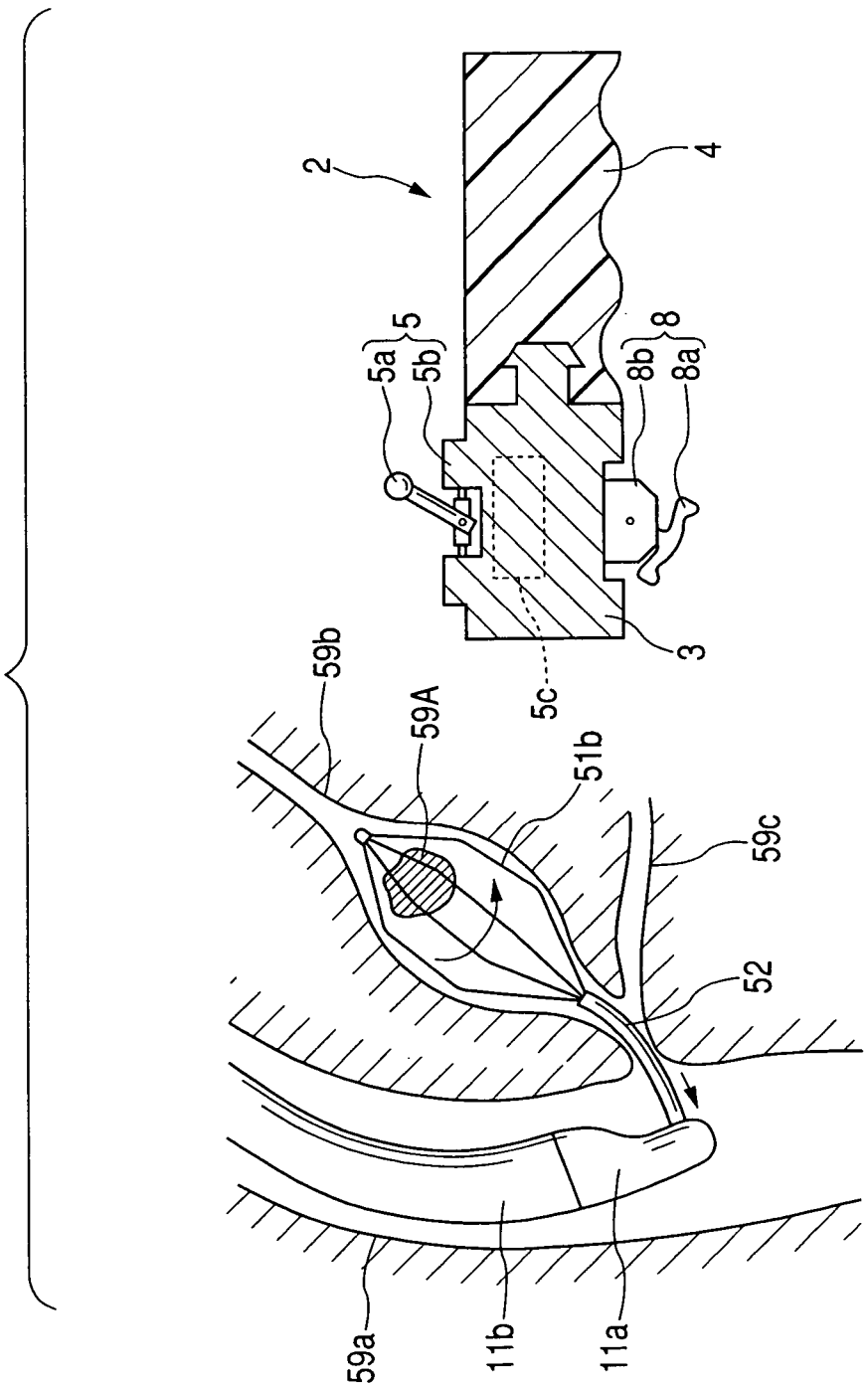

According to the present embodiment, as shown in FIGS. 23 and 24, the manipulating unit 2 is provided with a rotation commanding device 8, which is also an input device. This rotation commanding device 8 is mounted on a side of the outer surface different from the side on which the input device 5 is mounted. That is, the input device 5 and the rotation commanding device 8 are mounted on and jutted from the outer surface of the body 3 in the mutually opposite directions.

The rotation commanding device 8 is electrically connected to the controller 20 with the use of a signal cable 2a extended from the grip 4 of the manipulating unit 2. This rotation commanding unit 8 is composed of a rotation commanding lever 8a which can be tilted toward the direction perpendicular to the longitudinal axis of the manipulating unit 2 and a rotation commanding lever support 8b which supports the rotation commanding lever 8a.

According to the present embodiment, the controller 20 is provided with an A/D converter 122a, a motor controller 122b, and a motor driver 122c. The A/D converter converts to digital signals from the analogue signals transmitted from the manipulating unit 2 in response to tilt operations of the input device 5. This input device 5 is formed into a joystick type switch which is 2-axis operable and formed to have an auto origin-returning function. Tilting the rotation commanding lever 8a of the rotation commanding device 8 allows signals corresponding to the tilt to be transferred via the signal cable 2a. Then the A/D converter 122a sends the digital signals to the motor controller 122b, which controls the drive of the motor 44 of the instrument conveying unit 40 and the motors 36 and 38 of the instrument operating unit 30 depending on the above digital signals.

When the rotation commanding lever 8a is tilted in the forward direction, the motor controller 122b outputs electric control signals to the motor 38 of the instrument operating unit 30 for rotating it clockwise, for example. In contrast, when the rotation commanding lever 8a is tilted in the backward direction, the motor 38 is rotated counterclockwise.

Furthermore, setting is made such that the larger the amount of the tilt angle of the rotation commanding lever 8a, the higher the speed of rotation of the motor 38 of the instrument operating unit 30.

As a result, the endoscope system 1 of this embodiment is capable of rotating the sheath 52 of the instrument 50 together with the therapeutic member 51b (in this embodiment, basket), concurrently by the operator's tilting operation of the rotation commanding lever 8a of the rotation commanding device 8. The rotation commanding lever 8a is configured such that if this lever 8a is tilted in the forward direction, the sheath 52 and the therapeutic member 51b both is rotated clockwise, for example, when viewing the cross section of the sheath from the proximal end side of the sheath. In case that the rotation commanding lever 8a is tilted in the backward direction, the sheath 52 is rotated counterclockwise together with the therapeutic member 51b.

Therefore, in the same way as the manual operations in the first embodiment, an operator can manipulate the input device 5 using the thumb, for example. This operation allows the sheath 52 to be inserted and pulled back or the therapeutic member 51b (basket) to be expanded and contracted. Concurrently with this, the operator can use the first finger to manipulate the rotation commanding lever 8a to make the therapeutic member 51b rotate, together with the sheath 52, about the longitudinal axis of the sheath 52.

Specifically, tilting the rotation commanding lever 8a toward either the forward or backward direction, an analog signal responding to this tilt operation is sent to the controller 20 via the signal cable 2a. In the controller 20, the A/D converter 122a digitizes the analogue signal corresponding to the digital signal, which is then sent to the motor controller 122b. Depending on the digital signal, the motor controller 122b controls the drive of the motor 38 in the instrument operating unit 30 via the motor driver 122c.

The rotation of the motor 38 causes the gear 39 to rotate in a predetermined direction, which makes the sheath 52 rotate about the longitudinal axis of the sheath 52 inserted in the therapeutic-instrument channel 11CH by way of the gear 53a engaging with the gear 39. Incidentally, the rotational direction of the gear 39 is opposite to that of the gear 53a, so that the rotational direction of the motor 38 is opposite to a rotational direction along which the sheath 52 is rotated.

The rotational force of the sheath 52 is transmitted to the therapeutic member 51 arranged at the distal end thereof, resulting in that therapeutic member 51 is rotated in a predetermined direction. This predetermined direction is for example a counterclockwise direction (when viewing from the base end to the distal end) in response to a forward tilt of the rotation commanding lever 8a. By contrast, the predetermined direction is a clockwise direction in response to a backward tilt of the rotation commanding lever 8a. Of course, the opposite rotational functions to the above can be set to the lever 8a.

In the present embodiment, setting can be made such that the rotational speed of the sheath 52 and the therapeutic member 51b (that is, the basket) depends on an angular amount of a tilt of the rotational commanding lever 8a. Typically, the rotational speed is made faster as the tiled angle of the lever 8a from its initial position becomes deeper (larger).

In the endoscope system 1 of the present embodiment, the following operations and advantages can be obtained.

As shown in FIG. 23, similarly to the first embodiment, the sheath 52 is pulled out from the distal section 11a of the insertion tube 11 inserted in the duodena 59a, and then inserted into the bile duct 59b, during which time the therapeutic member 51b is expanded.

After this, as shown in FIG. 24, the operator tilts the operation lever 5a backward to insert the sheath 52 into the therapeutic-channel 11CH. And during this insertion, the operator tilts the rotation commanding lever 8a forward to rotate the therapeutic member 51b, that is, the basket, in the predetermined direction (e.g., the clockwise direction). This allows calculus 59A in the bile duct 59b to be taken in the basket. Then the operator is to tilt the operation lever 5a toward the tilt-direction marking "close" to make the basket to contract so that the calculus 59A is held firmly in the basket, before removing it from the bile duct 59b by pulling the basket.

As described, the endoscope system 1 according to the present embodiment is able to provide, in addition to the identical or similar advantages to those in the first embodiment, the rotation of the therapeutic member 51b. Further, the input device 5 and the rotation commanding device 8 (serving as the other input device), which are arranged at the symmetrical positions in the manipulating unit 2, are easier to handle by hand individually or at the same time.

Accordingly, the operator is able to manipulate the manipulating unit 2, which is at hand, to give commands to three operations of the therapeutic instrument 50, the three operations including the inserting/pulling-back operations of the sheath 52, the open/close operations of the therapeutic member 51b (i.e., the expansion and contraction of the basket in the present embodiment), and the rotation of the therapeutic member 51b.

Third Embodiment

Figure 25:
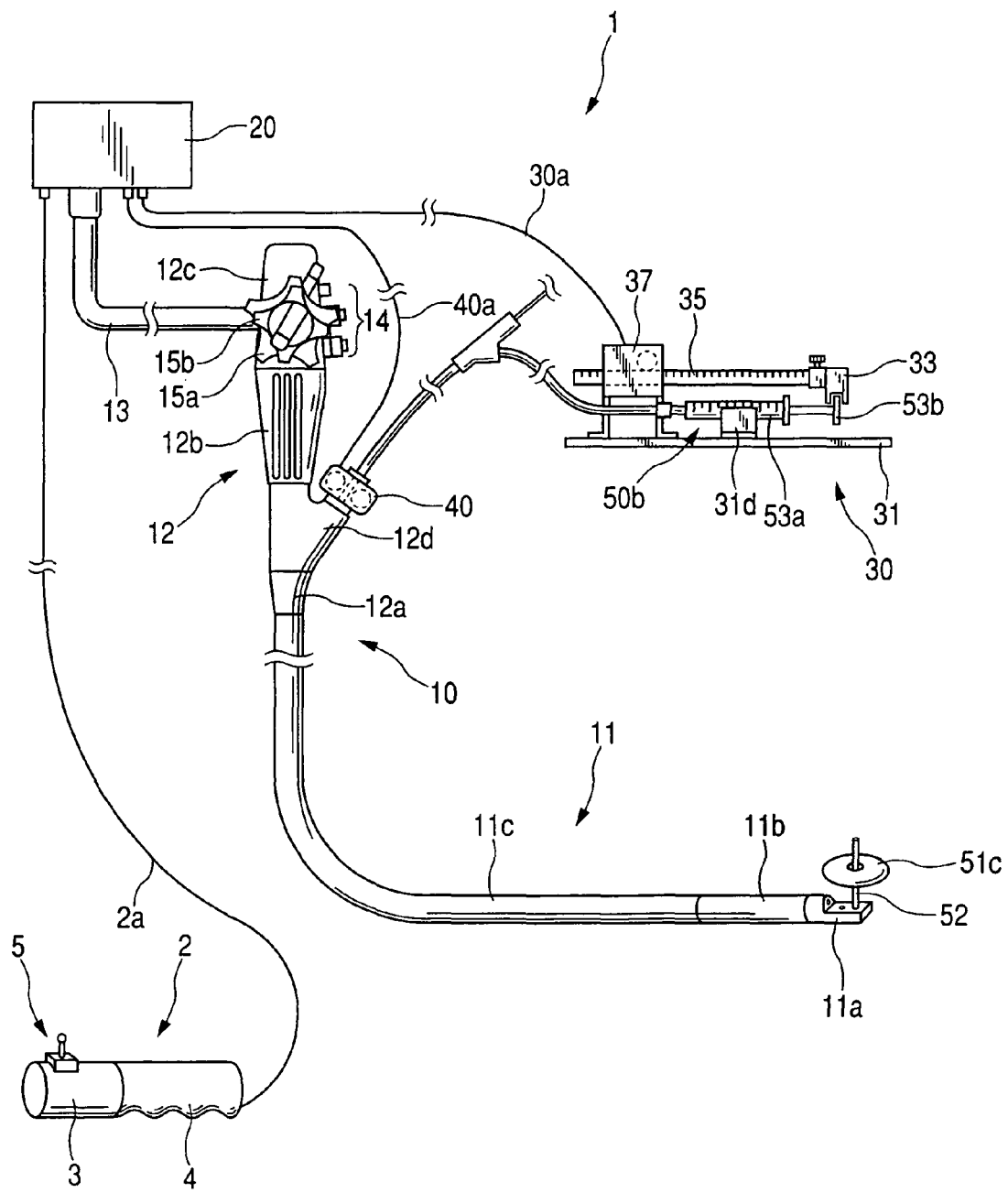
FIG. 25 is a schematic view showing the configuration of a main part of an endoscope system according to a third embodiment of the present invention.
Figure 26:
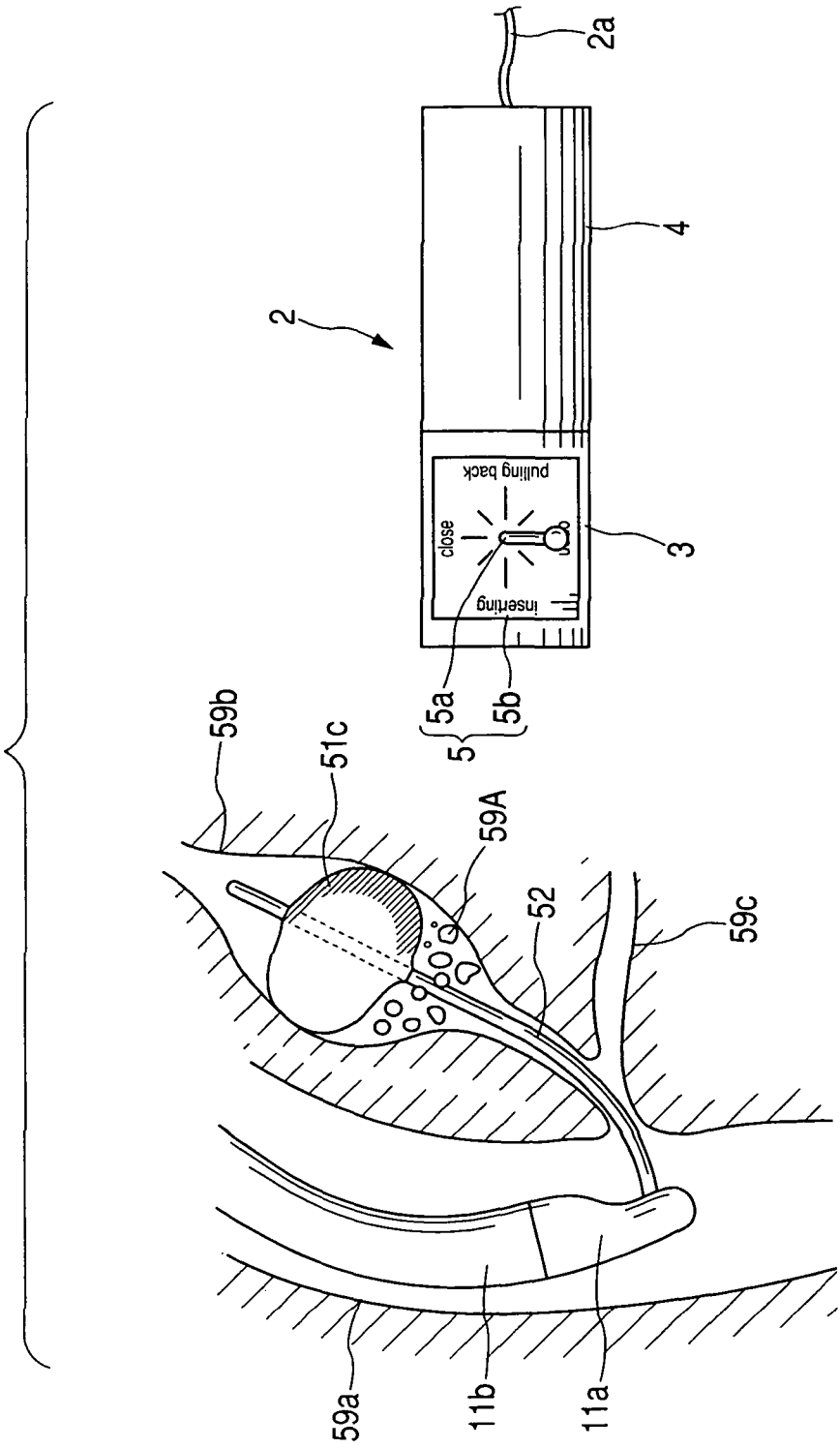
FIGS. 26 and 27 are illustrations each exemplifying how to manipulate an input device operating a balloon catheter serving as the therapeutic instrument.
Figure 27:
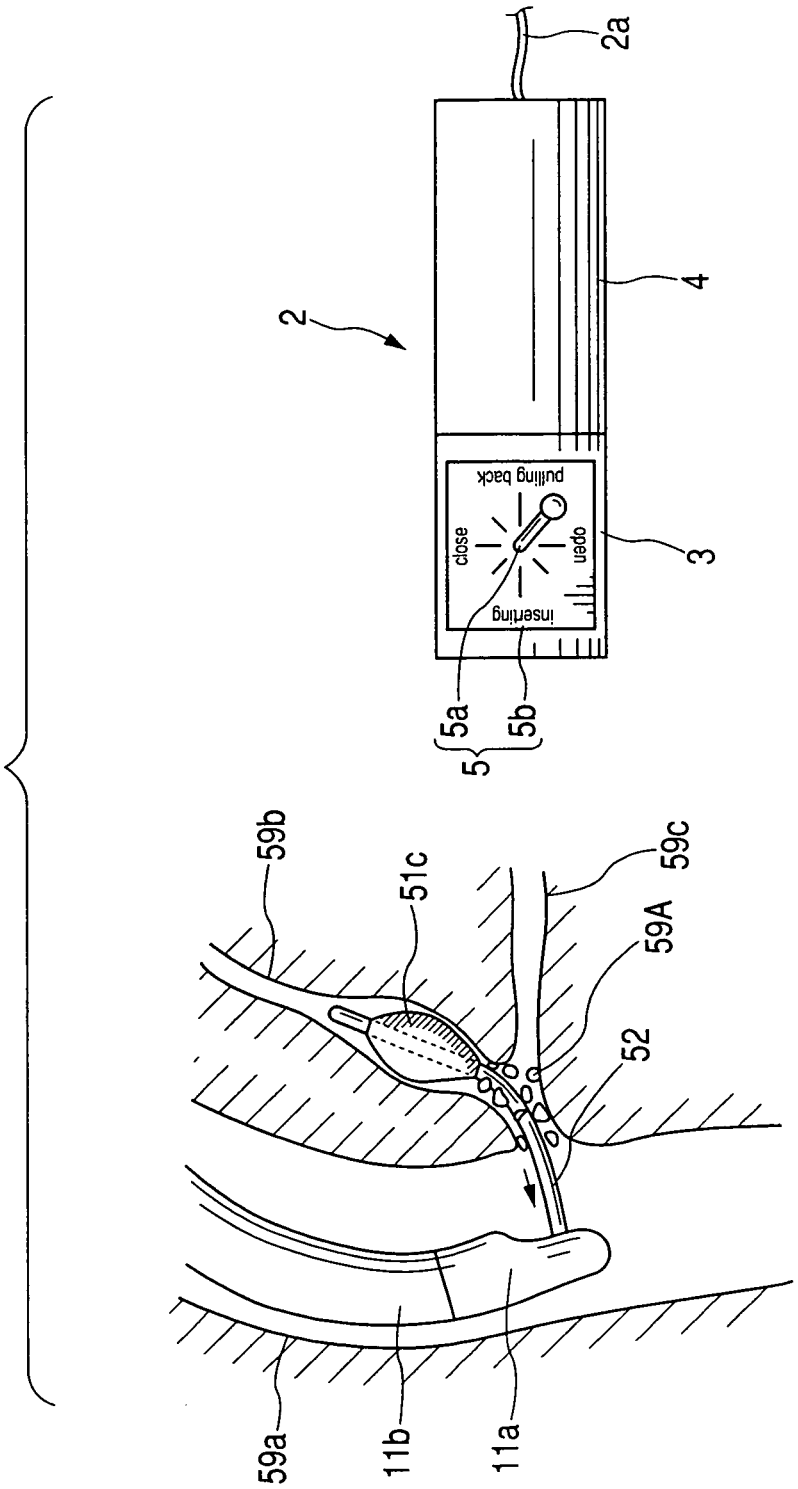

With reference to FIGS. 25-27, a third embodiment of the present embodiment will now be described.

The present embodiment exemplifies use of a balloon catheter also serving as the therapeutic instrument. The balloon catheter has the capability of collecting tiny calculus which is difficult to collect by the foregoing basket grasping forceps. In addition, the present embodiment employs a side-view type of endoscope 10.

As shown in FIG. 25, the endoscope system 1 employs a therapeutic instrument 50b in combination with the endoscope 10. The therapeutic instrument 50b has a syringe 53a at its base end and a balloon 51c disposed at the distal end of the sheath 52. The balloon 51c is made of elastic material. Moving a piston 53b permits fluid such as air in the syringe 53a to be injected into the balloon 51c via the sheath 52, thereby expanding the balloon 51c, that is, the therapeutic member.

In order to move the piston 53b forward and backward to the syringe 53a, the slider holding member 33 is fixed to a flange disposed at the base end of the piston 53b in the instrument operating unit 30. On the base 31 of this unit 30 is provided a fixing member 31b fixedly holding the syringe 53a.

Thus in response to a tilt of the operation lever 5a toward the marking "inserting" or "pulling back," the rack 35 is moved in the back-and-forth direction, which causes the piston 53b to be moved as well inside the syringe 53a in the axial direction thereof.

In this endoscope system 1, the insertion tube 11 of the endoscope 10 is inserted in the duodena 59a, and the sheath 52 of the therapeutic instrument 50b is placed into the bile duct 59b from a side window of the distal section 11a. As shown in FIG. 26, in response to an operator's tilt of the operation lever 5a toward the marking "open," fluid such as air is injected from the syringe 53a into a balloon 51c serving as the therapeutic member, so that the balloon 51c is expanded in the bile duct 59b.

Then, as show in FIG. 27, when the operator tilts the operation lever 5a toward the tilt-direction range between the markings "pulling-back" and "close," the sheath 52 is pulled back into the therapeutic-instrument 11CH, during which time the balloon 51c is contracted. Hence the operator is able to collect the tiny calculus 59A.

In this way, differently from the endoscope system 1 provided in each of the foregoing embodiment, the present endoscope system 1 can be adapted easily to the therapeutic instrument 50b such as a balloon catheter equipped with the syringe 53a. Thus, in the same way as the foregoing ones, the balloon catheter with the syringe 53a, which is also one of the various therapeutic instruments combined with the endoscope 10, can be used with ease.

Fourth Embodiment

A fourth embodiment of the present invention will now be described.

Figure 28:
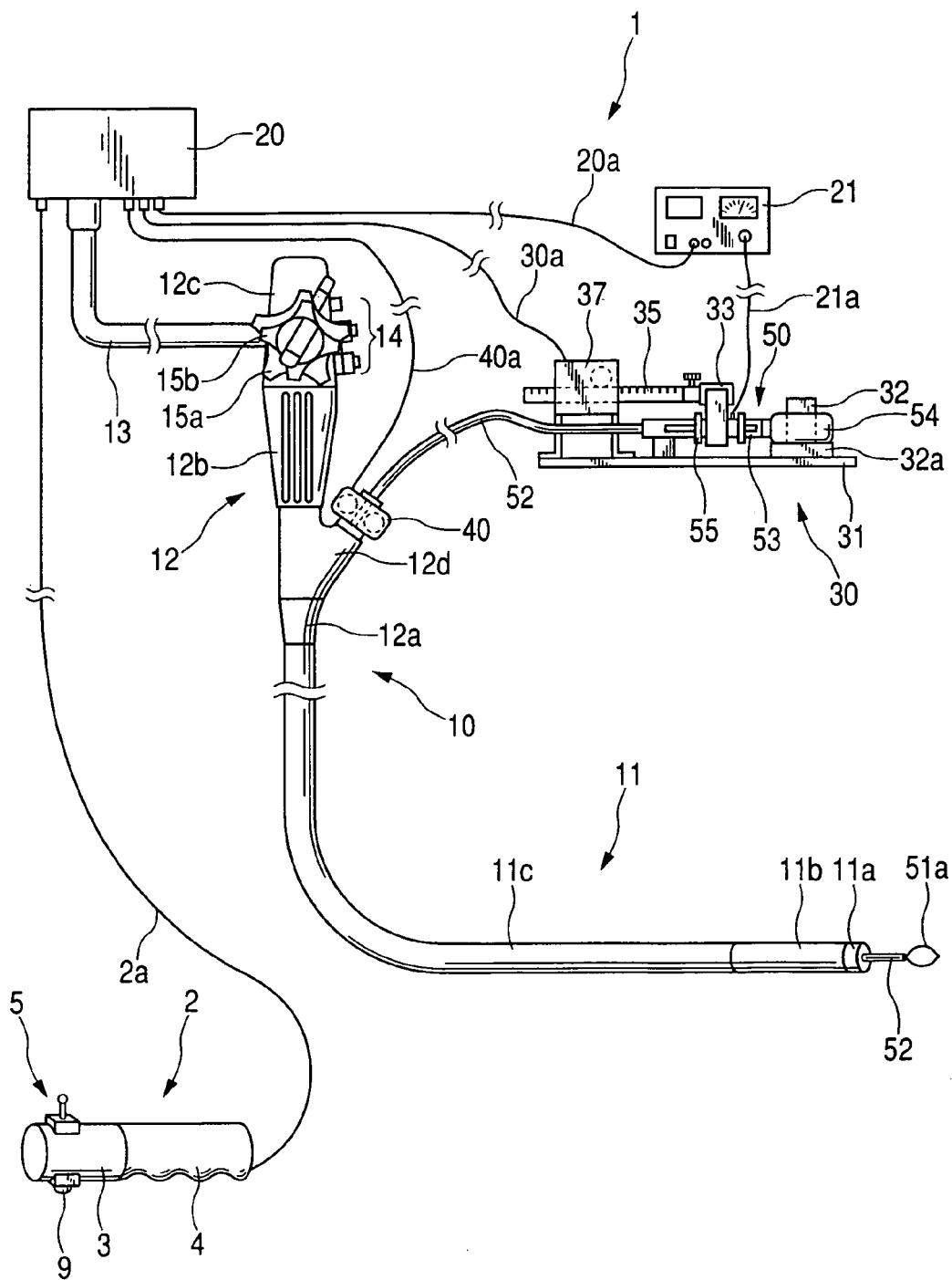
FIG. 28 is a schematic view showing the configuration of a main part of an endoscope system according to a fourth embodiment of the present invention.

As shown in FIG. 28, an endoscope 1 according to the present embodiment is provided with an endoscope 10, controller 20, and manipulating unit 2 for assisting the operations needed for the endoscope 10. This endoscope system 1 adopts, as a therapeutic instrument 50, an instrument for applying high-frequency-current-based therapy to lesions in body cavities. This kind of instrument includes a high-frequency surgical snare, hot biopsy forceps, and cautery knife. The present embodiment will now be exemplified with use of the high-frequency surgical snare.

The therapeutic instrument 50, which is the high-frequency surgical snare, is provided with the similar configurations to that in the first embodiment. Further, supplying high-frequency current to the therapeutic makes it possible that tissue inside a patient is cut open and/or blood stanching is performed on coagulation.

A high-frequency wire code 21a is used as an electrical connection between the therapeutic member 51a of the instrument 50 and a high-frequency power supply. The wire code 21a is connected, via the slider 55, to the metal connecting wire 52a passing through the sheath 52 and eclectically connected to the therapeutic member 51a.

Hence, high-frequency current is fed from the power supply 21 to the therapeutic member 51a via the wire code 21a. Meanwhile the high-frequency power supply 21 is communicably connected to the controller 20 via a communication cable 20*a* for control of power supply from the power supply 21.

Figure 43:
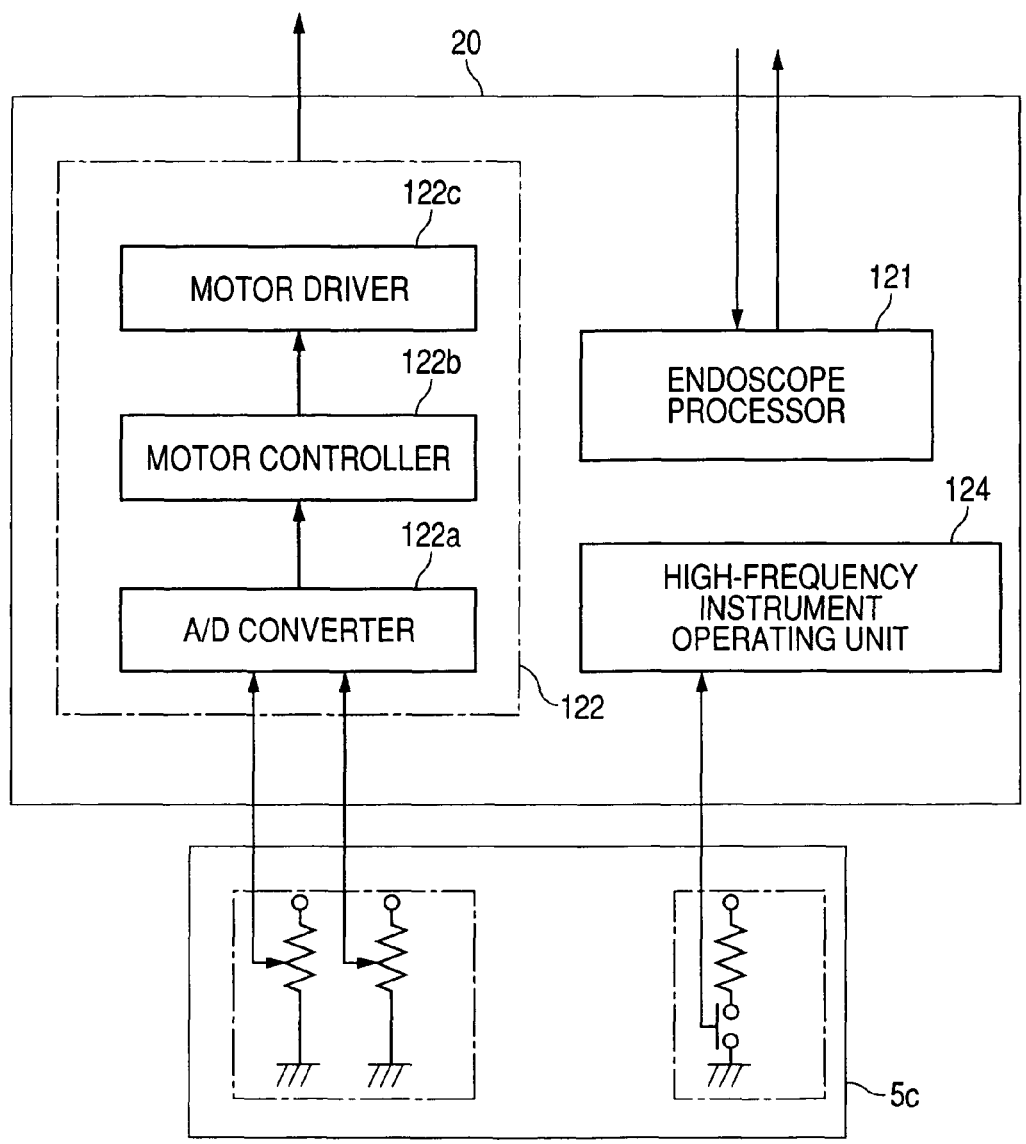
FIG. 43 is a functional block diagram showing a controller mounted in the endoscope system according to the fourth embodiment.
Figure 44:
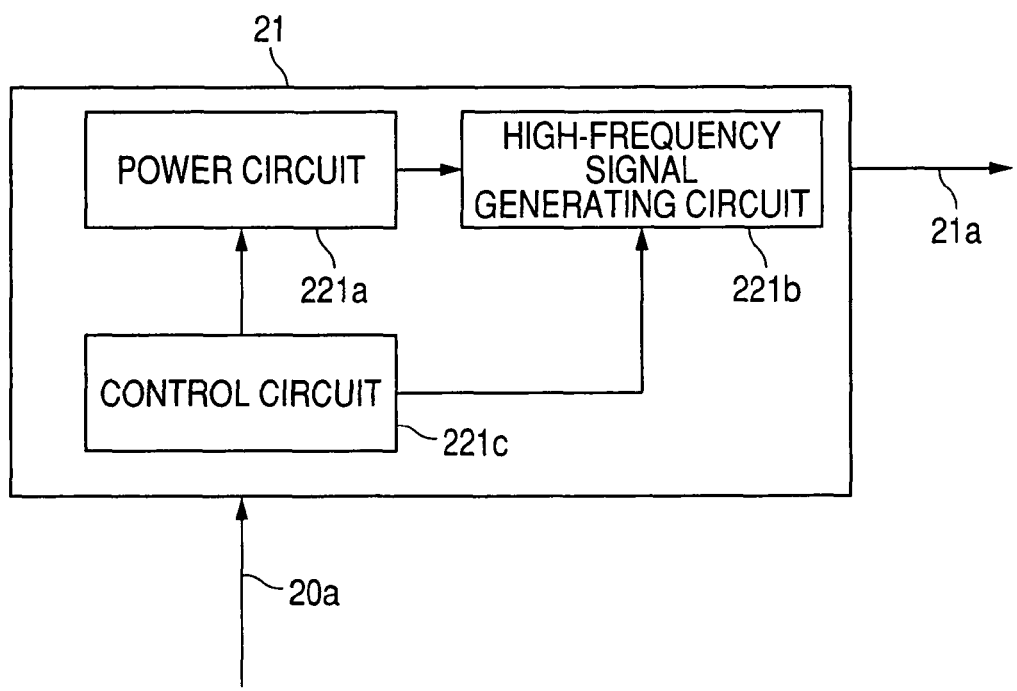
FIG. 44 is a functional block diagram showing a high-frequency power supply in the fourth embodiment.

As, shown in FIG. 43, the controller 20 is provided with a high-frequency instrument processor 124, in addition to the foregoing endoscope processor 121 and the motor control unit 122. The high-frequency instrument processor 124 receives command signals issued by the manipulating unit 2 via the signal cable 2*a* and transmits information instructed by the command signals, to the high-frequency power supply 21 as control signals. As shown in FIG. 44, in order to realize such operations, this power supply 21 is provided with at least a power circuit 221*a*, high-frequency signal generating circuit 221*b*, and control circuit 221*c*. The control signals, which come from the controller 20, are received through the communication cable 20*a* by the control circuit 221*c* of the power supply 21. The control circuit 221*c* provides both circuits 221*a* and 221*b* with currents depending on the control signals, with the result that high-frequency signals generated by the high-frequency signal generating circuit 221*b* is sent to the therapeutic member 51*a* of the therapeutic instrument 50 via the high-frequency wire code 21*a*.

As shown in FIG. 28, in the similar way to the foregoing various embodiments, the manipulating unit 2 is provided with the input device 5 protruded form one outer side of the body 3 and a high-frequency output switch 9 protruded from the other outer side of the body 3. The high-frequency output switch 9 serves another input device and is located at upper-and-lower different positions of the outer surface of the body 3.

The high-frequency output switch 9 may be equipped with a coagulation switch for supplying high-frequency current that is optimum in coagulating the living tissue, a cut-out switch for supplying high-frequency current that is optimum in cutting open the living tissue, and a dial that adjusts the output of the high-frequency current.

Accordingly, in the endoscope system 1 according to the present embodiment, the manipulating unit 2 is configured such that the input device 5 is used to operate the therapeutic instrument 50 and the high-frequency output switch 9 is used to provide the high-frequency current from the power supply 21 to the therapeutic instrument 50. In addition, the high-frequency current can be outputted to the therapeutic instrument 50 in parallel with or simultaneously with the operations to the input device 5.

As described, the endoscope system 1 can still enjoy the various advantages provided by the foregoing embodiments and can also have an advantage that the therapeutic instrument 50 using high-frequency current can be used well. The therapeutic instrument 50 is not limited to the high-frequency surgical snare, but may be hot biopsy forceps or cautery knife.

Modifications

Various modifications of the configurations described with the foregoing embodiments will now be described.

First Modification

Figure 29:
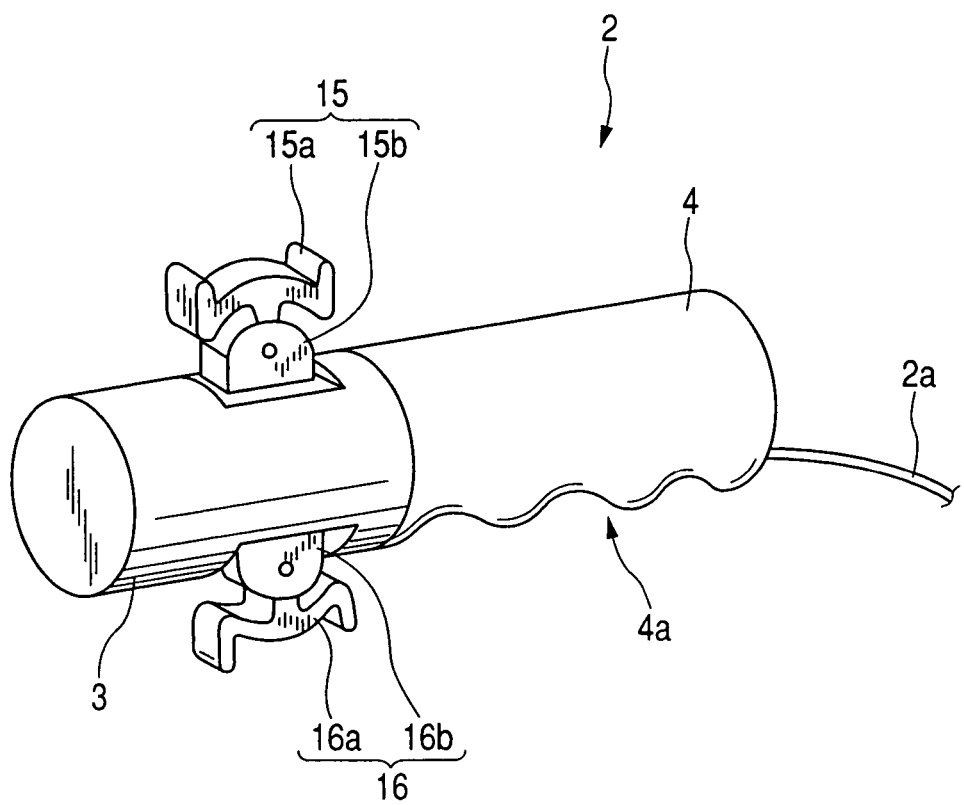
FIG. 29 is a perspective view showing an input device according to a first modification.
Figure 30:
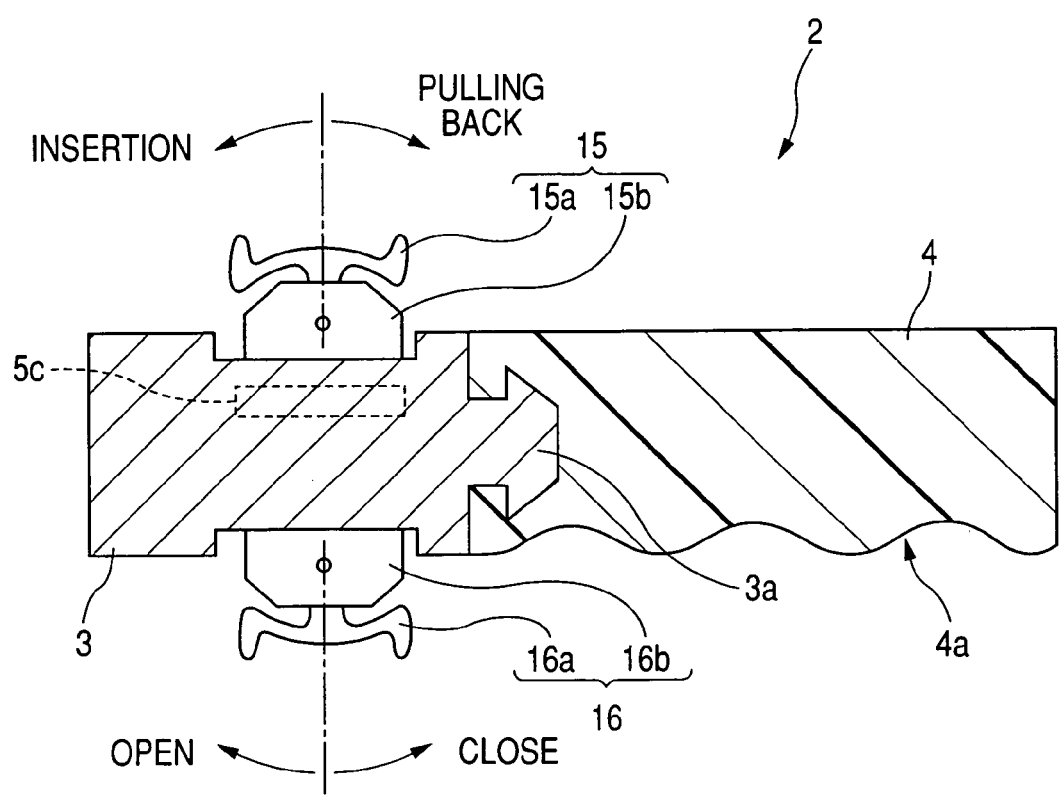
FIG. 30 is a cross sectional view showing the input device according to the first modification.
Figure 31:
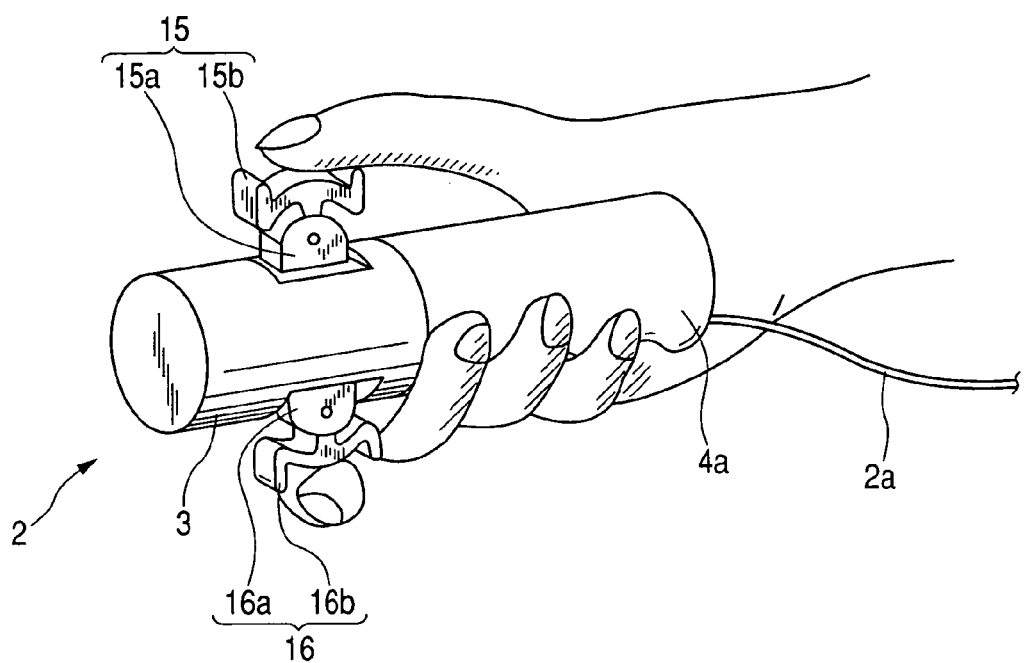
FIG. 31 illustrates how to operate the input device according to the first modification.

Referring to FIGS. 29 to 31, a first modification of the manipulating unit 2 will now be described.

As shown in FIGS. 29 and 30, a manipulating unit 2 according to the first modification is provided with input devices 15 and 16 on the upper and lower outer surface of the body 3 in FIG. 29, respectively. In this description, the upper and lower outer sides, which are opposed to each other with the body 3 therebetween, are defined in FIGS. 29 and 30.

The input device 15 arranged on the upper outer surface of the body 3 comprises an operation lever 15*a* and a lever supporting member 15*b* rotatably supporting the operation lever 15*a*. The operation lever 15*a* is operated along a single axis parallel to the longitudinal direction of the cylindrical body (body 3 and grip 4) of manipulating unit 2 and is for a lever moving back and forth the sheath 52 of the therapeutic instrument 50.

When an operator tilts the operation lever 15*a* forward, the sheath 52 is made to move so as to be inserted into the therapeutic-instrument channel 11CH by the instrument conveying unit 40. In contrast, when the operation lever 15*a* is tilted backward, the sheath 52 is made to move so as to be pulled out from the therapeutic-instrument channel 11CH by the instrument conveying unit 40.

Meanwhile the input device 16 arranged as an input device on the lower outer surface of the body 3 comprises an operation lever 16*a* and a lever supporting member 16*b* rotatably supporting the operation lever 16*a*. This operation lever 16*a* is operated along a single axis parallel to the longitudinal direction of the cylindrical body (body 3 and grip 4) of manipulating unit 2 and is in charge of opening/closing the therapeutic member 51 or bending the therapeutic member 51 upward and downward.

In response to an operator's forward tilt of the operation lever 16*a*, the instrument operating unit 30 causes the slider 55 to move in one desired tilt-direction the handle 53 of the therapeutic instrument 50, which makes the therapeutic member 51 open (or bend upward). In contrast, responsively to an operator's backward tilt of the operation lever 16*a*, the instrument operating unit 30 causes the slider 55 to move in the remaining desired direction along the handle 53 of the therapeutic instrument 50, which makes the therapeutic member 51 close (or bend downward).

Of course, the inserting/pulling-out operations of the sheath 52 or the open/close (or bending upward/downward) operations of the therapeutic member 51 may be assigned to the input devices in an opposite way to the above. In such a case, of both operation levers 15*a* and 16*a*, one lever 15*a* is used for the open/close (bending) operations of the therapeutic member 51, while the other lever 16*a* is used for inserting/pulling out the sheath 52.

As shown in FIG. 31, the thus-constructed manipulating unit 2 is gripped by an operator by one hand, in which, for example, the operation lever 15*a* is touched by the thumb and the operation lever 16*a* is touched by the first finger such that both levers 15*a* and 16*a* are tiled separately from each other.

As described above, the manipulating unit 2 according to the first modification is different in configuration from the foregoing embodiments in which one input switch 5 is in charge of the inserting/pulling-back operations of the sheath 52 and the opening/closing (bending) operations of the therapeutic member 51 and is configured to have the two input devices 15 and 16 each assigned to part of the operations of the therapeutic instrument 50. As a result, the manipulating unit 2 still provides the similar advantages to the foregoing ones, without losing the good operationality of the therapeutic instrument 50

Second Modification

Referring to FIGS. 32 to 35, a second modification of the manipulating unit 2 will now be described.

Figure 32:
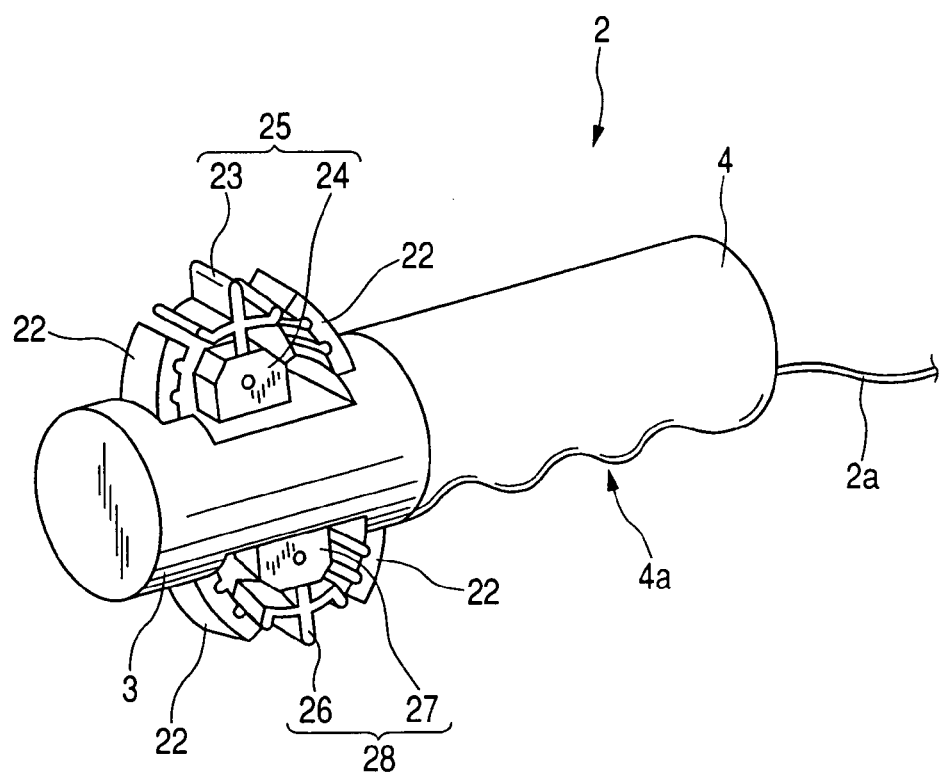
FIG. 32 is a perspective view showing an input device accruing to a second modification.
Figure 33:
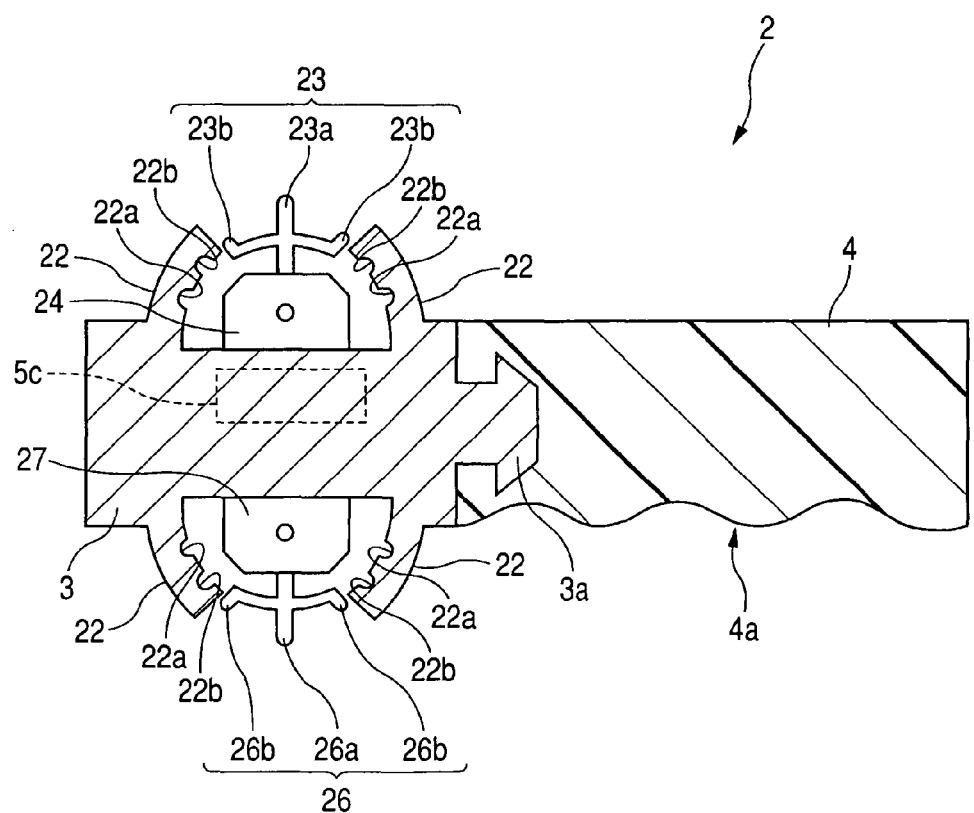
FIG. 33 is a longitudinal cross sectional view of the input device according to the second modification.

As shown in FIGS. 32 and 33, a manipulating unit 2 according to the second modification is provided with two input devices 25 and 28 on the upper and lower outer surfaces of the body 3, respectively. This unit 2 is still provided with two pairs of lever lock members 22 each pair of which is protruded from the outer surface and is located so that each input device is placed between two parts of each pair of lever lock members 22 in the longitudinal direction of the body 3, i.e., the unit 2. Each of the two paired lock members 22 is for locking each input device.

Each of the input devices 25 and 28 is provided with an operation lever 23 (28) and a lever supporting member 24 (27), similarly to the first modification. Each operation lever 23 (28) comprises, as shown in FIG. 33, an operation shaft 23a (26a) having an approximate cross section in the longitudinal direction of the body 3. Each of the operation shafts 23a and 26a includes an arch-like arm portion extending in the longitudinal direction so as to make a crossed form with the shaft 23a (26a). Both ends of the arch-like arm portion are formed to have protrusions 23b and 26b. In this case, the input device 25 is for inserting/pulling back the sheath 52, while the input device 28 is for opening/closing (bending) the therapeutic member 51.

Each pair of lever lock members 22, consisting of two arch-shaped portion, are protruded from the outer surface to sandwich each lever 23 (26) in the longitudinal direction. Each arch-shaped portion has two mutually-parallel locking grooves 22a and 22b formed on the inner surface in the direction perpendicular to the longitudinal direction. The two locking grooves 22a and 22b are arranged in the order of 22a to 22b from a side near to the outer surface of the body 3. The number of locking grooves may be one or three or more, not limited to two.

Figure 34:
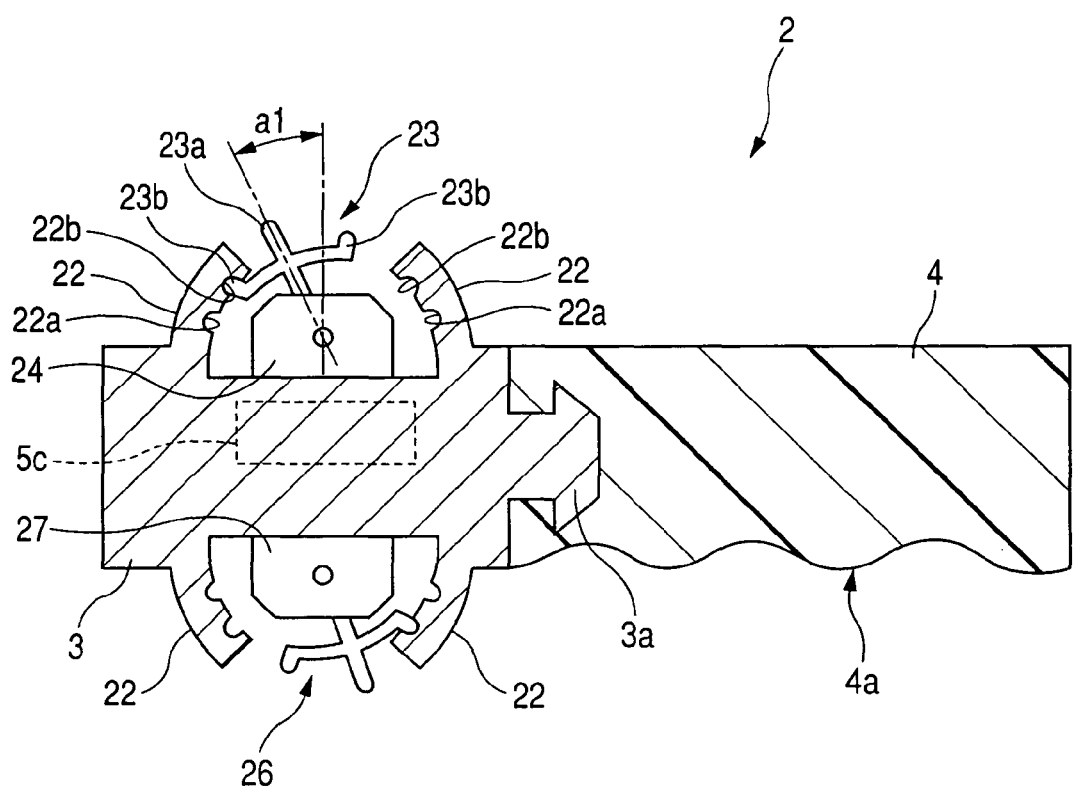
FIGS. 34 and 35 illustrate a locking function of tilt angels in the input device according to the second modification.
Figure 35:
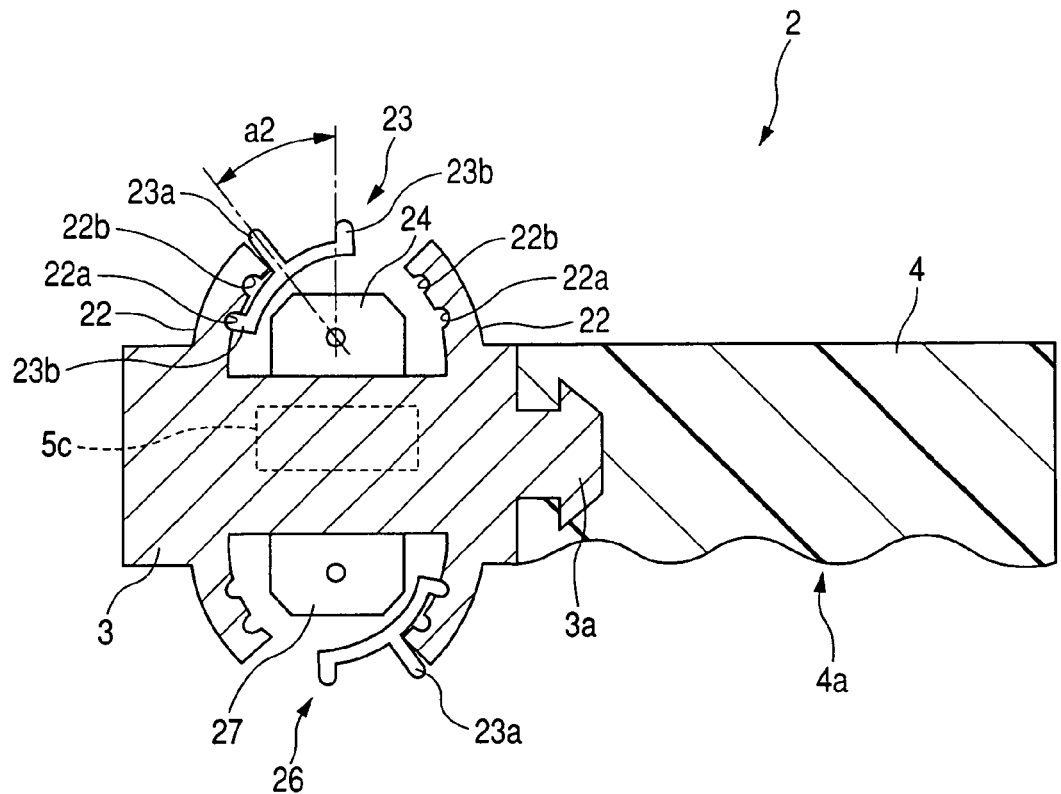

Thus, in the present manipulating unit 2, as shown in FIGS. 34 and 35, the operation levers 23 and 26 can be tiled and locked at their tilted positions.

To be specific, as illustrated in FIG. 34, the operation lever 23 is tilted forward and, at its tilted position, the protrusion 23b is fit in the first locking groove 22b, whereby the operation shaft 23a is held at a first angle α1 from its initial portion. This locked operation allows the sheath 52 to be inserted through the therapeutic-instrument channel 11CH at a first constant speed.

Further, as illustrated in FIG. 35, the operation lever 23 is tilted more deeply in the forward direction so that the protrusion 23b is fit in the second locking groove 22a, whereby the operation shaft 23a is held at a second angle α2 (>α1) from its initial potion. Responsively to this deeper tilt, the sheath 52 is inserted through the therapeutic-instrument channel 11CH at a second constant speed faster than the first constant speed.

Similarly to the above, the other operation lever 26 can be tilted and locked at its tilted angle (α1, α2). It is therefore possible to alter the open/close (or bending) speed of the therapeutic member 51 and a grip force (or bending angle).

As a result, once one or both of the operation levers 23 and 26 are tilted and locked, the manipulating unit 2 can still be manipulated even if the operator releases the fingers from the operation levers 23 and 26. In this hand-free state, the sheath 52 is conveyed at a constant speed and the therapeutic member 51 is opened/closed (bent) at a constant seed and kept at its constant grip force (bending angle).

Third Modification

Figure 36:
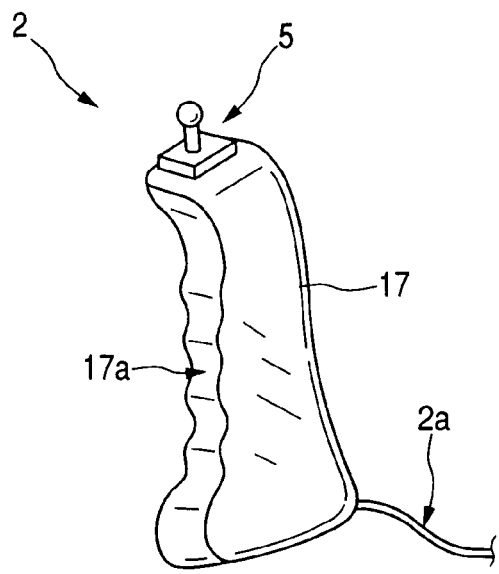
FIG. 36 is a perspective view showing an input device accruing to a third modification.
Figure 37:
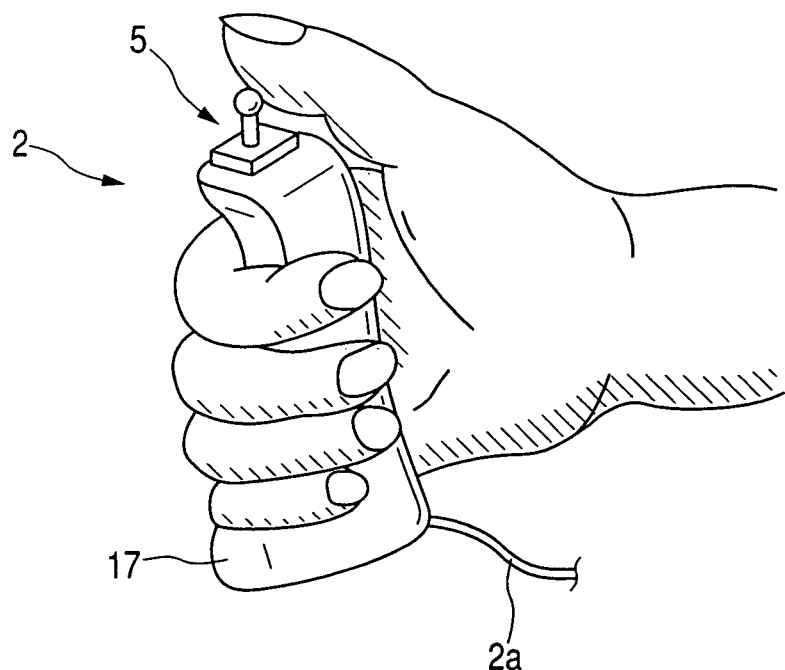
FIG. 37 illustrates how to grip and manipulate the input device according to the third modification.

Referring to FIGS. 36 to 37, a third modification of the manipulating unit 2 will now be described.

As shown in FIG. 36, a manipulating unit 2 according to the third modification comprises a stick member 17 with a gripping surface 17a formed on the front and an input device 5 capable of commanding the operations of the therapeutic instrument 50 mounted at the top of the stick member 17 so as to protrude therefrom. The input device 5 is configured to be operable in two axes and eclectically connected to an electric cable 2a which is drawn from a base portion on the back.

This manipulating unit 2 can be held as shown in FIG. 37, where the stick member 17 is gripped by four fingers other than the thumb and the input device 5 is operated by the thumb, for instance. Hence this modification provides the identical operations and advantages to the foregoing embodiments.

Fourth Modification

Figure 38:
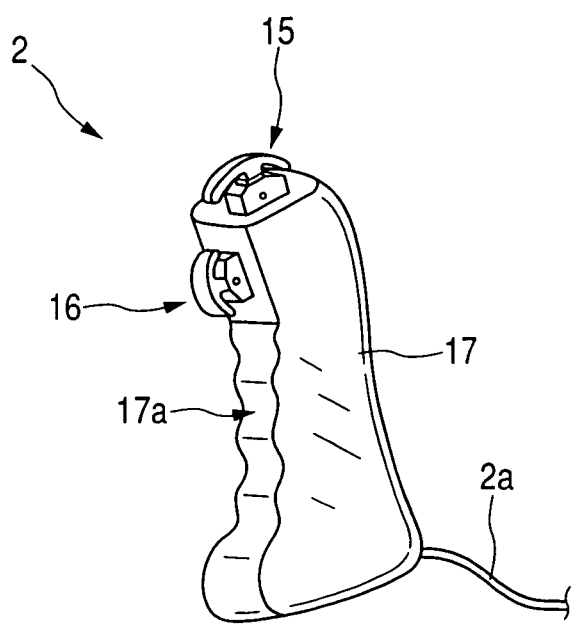
FIGS. 38 and 39 are perspective and side views each showing an input device accruing to a fourth modification, respectively.
Figure 39:
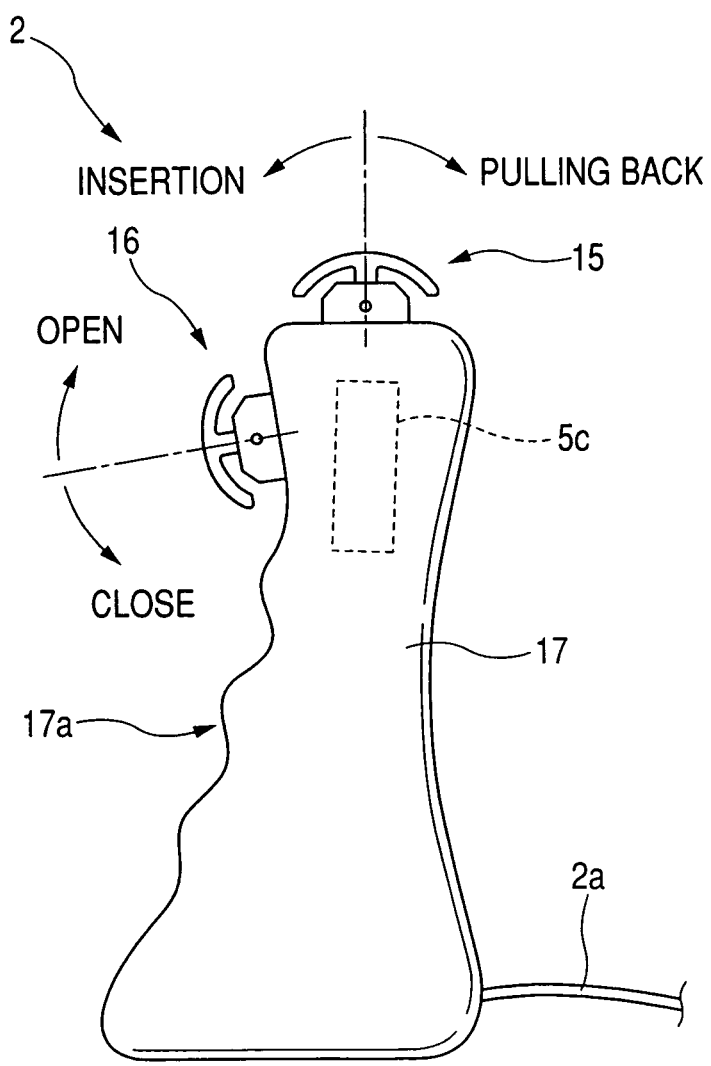
Figure 40:
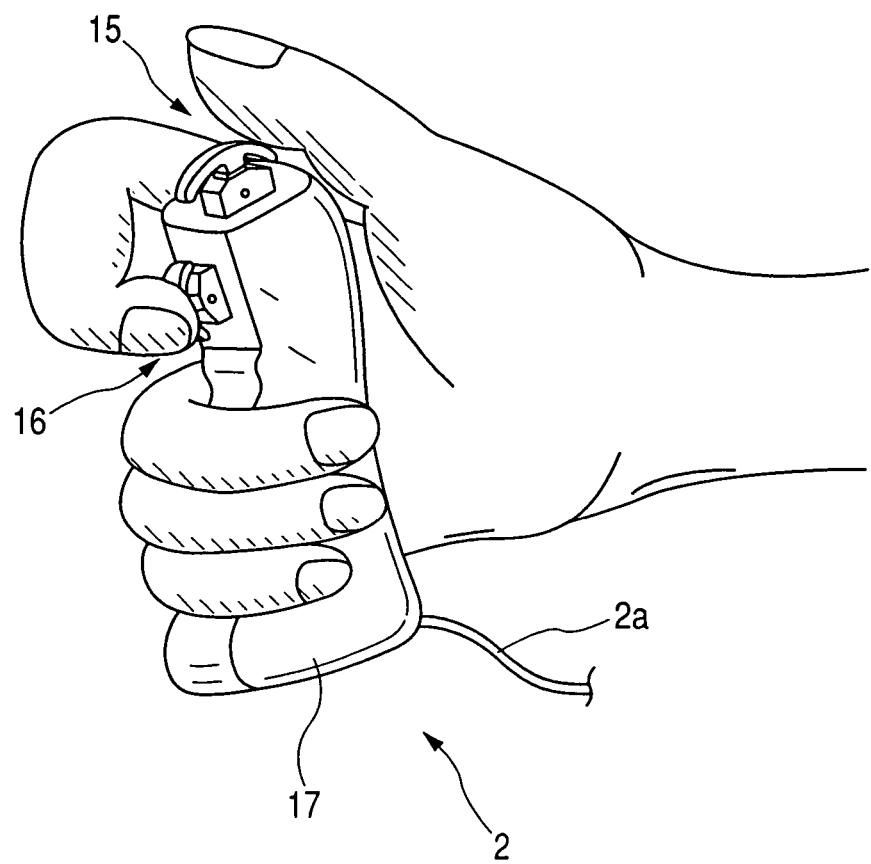
FIG. 40 illustrates how to grip and manipulate the input device according to the fourth modification.

Referring to FIGS. 38 to 40, a fourth modification of the manipulating unit 2 will now be described.

As shown in FIG. 38, a manipulating unit 2 according to the fourth modification comprises two input devices 15 and 16, which are mounted at the stick member 17 adopted by the foregoing third modification. Each input device 15 (16) is operable on the single axis motion but still enables either the inserting/pulling-back operation of the sheath 52 or the open/close (bending) operation of the therapeutic member 51.

Specifically, as is clearer from FIG. 39, of the two input devices 15 and 16, one input device 15 for inserting/pulling-back the sheath 52 is mounted at the top of the stick member 17, while the remaining input device 16 for opening/closing (bending) the therapeutic member 51 is mounted at an upper-side position on the front of the stick member 17. As a matter of course, the operations to be assigned to both input devices 15 and 16 may be opposite to each other.

As illustrated in FIG. 40, this manipulating unit 2 is also gripped by an operator by one hand, where the stick member 17 is held by almost three fingers other than the thumb and the first finger which operate both input devices 15 and 16. Hence the unit 2 can be operated similarly to the foregoing embodiments to obtain the similar advantages to those.

By the way, the input devices 5, 15, 16, 25 and 28 explained in the foregoing embodiments and modifications are designed to be operable in the single- or two-axis motions for operating the therapeutic instrument 50. However this is not a definitive example. These input devices may be designed to be operable in three- or four-axis motions, so that operations of other therapeutic instruments, which are for example, operations for supply of high-frequency current and selection between a coagulation mode and a cutting-open mode, may be assigned to remaining axial motions. By way of example, the three-axis operations can be set to switching operations including pushing operations of an operation lever (for example, the lever 5) along an axis and rotating operations to make a switch on/off, whilst the four-axis operations can be set to switching operations including pushing operations of an operation lever (for example, the lever 5) along an axis and rotating operations to make two switches on/off respectively.

Furthermore, the present invention is not limited to the foregoing configurations in which the operation assisting apparatus is functionally combined with an endoscope system, but may be modified into other forms. Objects to be manipulated can be developed to the operations of the endoscope itself. For example, various operations of an endoscope, such as banding operations, operations for various optical systems, and operations for air supply and water supply, as well as operations of the therapeutic instruments, can be performed under the manual operations at the manipulating unit. The endoscope and/or therapeutic instrument may be remote-controlled from the foregoing manipulating units.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. An endoscope system, comprising:
    an endoscope including:
        a tubular portion having a distal end;
        a therapeutic member attached to the distal end of the tubular portion for a desired therapeutic treatment; and
        an insertion tube including a channel through which the tubular portion and the therapeutic member are inserted;
    a first drive unit which drives the therapeutic member in response to a first command signal;
    a second drive unit fixedly and directly connected to an inlet structure of the endoscope and which drives the tubular portion in response to a second command signal;
    an input device including a single input member; and
    a controller electrically connected to the input device by a single cable transmitting first and second command signals, the controller further including a single driver which provides the first and second drive units with the first and second command signals, respectively, based on a single input operation of the single input member of the input device, to control the first and second drive units according to one of the three control modes wherein
    the three control modes include:
        a first control mode in which, based on a first input operation of the single input member of the input device, the second drive unit is driven to apply force to the tubular portion in the direction in which the tubular portion advances forward or goes back, and the first drive unit is driven to apply force to the therapeutic member in the direction in which the therapeutic member advances forward or goes back, whereby the tubular portion advances forward or goes back together with the therapeutic member;
        a second control mode in which, based on a second input operation of the single input member of the input device, the second drive unit is driven to apply force to the tubular portion in the direction in which the tubular portion advances forward, and the first drive unit is driven to apply force to the therapeutic member so as to be fixed with respect to the tubular portion at a position in the longitudinal direction of the tubular portion, whereby the tubular portion advances forward in a state where the therapeutic member remains essentially at the same position; and
        a third control mode in which, based on a third input operation of the single input member of the input device, the first drive unit is driven to apply force to the therapeutic member in the direction in which the therapeutic member goes back, and the second drive unit is driven to apply force to the tubular portion so as to be fixed with respect to the therapeutic member at a position in the longitudinal direction of the tubular portion, whereby the therapeutic member goes back in a state where the tubular portion remains essentially at the same position.

2. The endoscope system of claim 1, wherein
    the input device further includes an output member,
    the input member is adapted to be manually actuated to cause the output member to generate both kinds of commands for driving both the therapeutic member and the tubular portion simultaneously depending on a predetermined input position obtained after the manual actuation, and
    the output member outputs the commands to the controller.

3. The endoscope system of claim 2, wherein the output member is configured to output commands indicating an operation speed of the therapeutic member and a conveyance speed of the tubular portion to the controller depending on an actuation position of the input member.

4. The endoscope system of claim 1, wherein the input member is further adapted to be operated to cause the output member to generate commands for driving the therapeutic member and the tubular portion separately, and the output member is adapted to output the commands to the controller such that the therapeutic member and the tubular portion are driven separately.

5. The endoscope system of claim 4, wherein the output member is configured to output commands indicating an operation speed of the therapeutic member and a conveyance speed of the tubular portion to the controller depending on an actuation position of the input member.

6. The endoscope system of claim 1, wherein
    the input device is arranged at part of a gripper gripped by an operator, and
    the input device is protruded from the gripper.

7. The endoscope system of claim 6, wherein the input device is structured to have a lever operable about an axis of the lever.

8. The apparatus of claim 6, wherein the input device comprises a switch to output the commands and the gripper is formed to have stick-like shape.

9. The endoscope system of claim 7, wherein the lever is operable about either one or two axes of the lever.

10. The endoscope system of claim 6, wherein
    the gripper has a substantially cylindrical appearance adaptive to an operator's grip, and
    the input device is formed so as to be actuated by a finger of the operator who grips the gripper.

* * * * *